US012606802B2

(12) United States Patent
Maurer et al.

(10) Patent No.: US 12,606,802 B2
(45) Date of Patent: Apr. 21, 2026

(54) METHODS AND COMPOSITIONS FOR IMPROVING THE ASSEMBLY OF ADENO-ASSOCIATED VIRUSES (AAVS)

(71) Applicants: Massachusetts Eye & Ear Infirmary, Boston, MA (US); The Schepens Eye Research Institute, Inc., Boston, MA (US)

(72) Inventors: Anna C. Maurer, Boston, MA (US); Luc H. Vandenberghe, Weston, MA (US)

(73) Assignees: Massachusetts Eye and Ear Infirmary, Boston, MA (US); The Schepens Eye Research Institute, Inc., Boston, MA (US)

( * ) Notice: Subject to any disclaimer, the term of this patent is extended or adjusted under 35 U.S.C. 154(b) by 1060 days.

(21) Appl. No.: 17/603,221

(22) PCT Filed: Apr. 13, 2020

(86) PCT No.: PCT/US2020/028015
§ 371 (c)(1),
(2) Date: Oct. 12, 2021

(87) PCT Pub. No.: WO2020/210839
PCT Pub. Date: Oct. 15, 2020

(65) Prior Publication Data
US 2022/0186193 A1 Jun. 16, 2022

Related U.S. Application Data

(60) Provisional application No. 62/833,595, filed on Apr. 12, 2019.

(51) Int. Cl.
*C12N 7/00* (2006.01)

(52) U.S. Cl.
CPC ...... *C12N 7/00* (2013.01); *C12N 2750/14152* (2013.01)

(58) Field of Classification Search
CPC ..................... C12N 7/00; C12N 2750/14152
See application file for complete search history.

(56) References Cited

U.S. PATENT DOCUMENTS

| | | | | |
|---|---|---|---|---|
| 11,661,581 B2 * | 5/2023 | Socolovsky | ........... | A61K 35/18 424/93.73 |
| 2005/0233963 A1 | 10/2005 | Moseley et al. | | |
| 2005/0271639 A1 * | 12/2005 | Penn | .................... | A61K 38/193 435/366 |
| 2007/0275918 A1 * | 11/2007 | Kiyokawa | ............ | A61K 31/713 435/375 |
| 2012/0028357 A1 | 2/2012 | Urabe et al. | | |
| 2017/0029785 A1 | 2/2017 | Zhao et al. | | |
| 2017/0165348 A1 * | 6/2017 | Cantore | .................. | A61P 17/04 |
| 2018/0327752 A1 | 11/2018 | Pillay et al. | | |
| 2018/0340148 A1 | 11/2018 | Socolovsky et al. | | |
| 2021/0269828 A1 * | 9/2021 | Samulski | ............... | C12N 15/86 |
| 2022/0186255 A1 * | 6/2022 | Godia-Casablancas | .................... | C12N 15/86 |

FOREIGN PATENT DOCUMENTS

| | | | | |
|---|---|---|---|---|
| CN | 105980551 A | 9/2016 | | |
| WO | WO-0219965 A2 * | 3/2002 | ........... | A61K 31/352 |
| WO | WO 2020/210839 A1 | 10/2020 | | |

OTHER PUBLICATIONS

Fontaine, S. et al. (2016). DnaJ/Hsc70 chaperone complexes control the extracellular release of neurodegenerative-associated proteins. The EMBO Journal, 35(14), 1537-1549. (Year: 2016).*
Jinwal, U. K., (2013). Imbalance of Hsp70 family variants fosters tau accumulation. FASEB journal : official publication of the Federation of American Societies for Experimental Biology, 27(4), 1450-1459. (Year: 2013).*
Maurer, A. C., Pacouret, S., Cepeda Diaz, A. K., Blake, J., Andres-Mateos, E., & Vandenberghe, L. H. (2018). The Assembly-Activating Protein Promotes Stability and Interactions between AAV's Viral Proteins to Nucleate Capsid Assembly. Cell Reports (Cambridge), 23(6), 1817-1830. (Year: 2018).*
Nakamura, K., Yokoyama, N., & Igarashi, I. (2007). Cyclin-dependent kinase inhibitors block erythrocyte invasion and intraerythrocytic development of Babesia bovis in vitro. Parasitology, 134(10), 1347-1353. (Year: 2007).*
Ko et al. (2015). A small molecule inhibitor of ATPase Activity of HSP70 Induces Apoptosis and Has Antitumor Activities. Chemistry & Biology, 22(3), 391-403. (Year: 2015).*
EP 20787242.5, Sep. 22, 2022, European Search Report and Written Opinion.
PCT/US2020/028015, Jul. 31, 2020, International Search Report and Written Opinion.
PCT/US2020/028015, Sep. 28, 2021, International Preliminary Report on Patentability.
Aponte-Ubillus et al., A rAAV2-producing yeast screening model to identify host proteins enhancing rAAV DNA replication and vector yield. Biotechnol Prog. Jan. 2019;35(1):e2725. doi: 10.1002/btpr. 2725. Epub Oct. 2, 20182.
Aponte-Ubillus, Optimization of Recombinant Adeno-Associated Virus (aav) Vector Production in Saccharomyces Cerevisiae, KGI Theses and Dissertations, Jan. 1, 2018; 8:1-162. https://scholarship.claremont.edu/kgi_theses/8.
Barajas et al., Generation of infectious recombinant Adeno-associated virus in Saccharomyces cerevisiae. PLoS One. Mar. 29, 2017;12(3):e0173010. doi: 10.1371/journal.pone.0173010. eCollection 2017.

(Continued)

*Primary Examiner* — Janet L Andres
*Assistant Examiner* — Carey Alexander Stuart
(74) *Attorney, Agent, or Firm* — Wolf, Greenfield & Sacks, P.C.

(57) ABSTRACT

Described herein are methods and compositions for modifying cells to improve the assembly of adeno-associated viruses (AAVs).

18 Claims, 19 Drawing Sheets

(56)                    References Cited

OTHER PUBLICATIONS

Cheng et al., Molecular basis for viral selective replication in cancer cells: activation of CDK2 by adenovirus-induced cyclin E. PLoS One. 2013;8(2):e57340. doi: 10.1371/journal.pone.0057340. Epub Feb. 20, 2013.

Chung et al., Cdk2 is required for p53-independent G2/M checkpoint control. PLoS Genet. Feb. 26, 2010;6(2):e1000863. doi: 10.1371/journal.pgen.1000863.

Costello et al., High mobility group chromosomal protein 1 binds to the adeno-associated virus replication protein (Rep) and promotes Rep-mediated site-specific cleavage of DNA, ATPase activity and transcriptional repression. EMBO J. Oct. 1, 1997;16(19):5943-54. doi: 10.1093/emboj/16.19.5943.

Douar et al., Intracellular trafficking of adeno-associated virus vectors: routing to the late endosomal compartment and proteasome degradation. J Virol. Feb. 2001;75(4):1824-33. doi: 10.1128/JVI.75.4.1824-1833.2001.

Ni et al., Cellular proteins required for adeno-associated virus DNA replication in the absence of adenovirus coinfection. J Virol. Apr. 1998;72(4):2777-87. doi: 10.1128/JVI.72.4.2777-2787.1998.

Satkunanathan et al., Establishment of a novel cell line for the enhanced production of recombinant adeno-associated virus vectors for gene therapy. Hum Gene Ther. Nov. 2014;25(11):929-41. doi: 10.1089/hum.2014.041. Epub Sep. 11, 2014.

Mano et al., Genome-wide RNAi screening identifies host restriction factors critical for in vivo AAV transduction. Proc Natl Acad Sci U S A. Sep. 8, 2015;112(36):11276-81. doi: 10.1073/pnas.1503607112. Epub Aug. 24, 2015.

Zhou et al., Long-term protection against human papillomavirus e7-positive tumor by a single vaccination of adeno-associated virus vectors encoding a fusion protein of inactivated e7 of human papillomavirus 16/18 and heat shock protein 70. Hum Gene Ther. Jan. 2010;21(1):109-19.

* cited by examiner (Enriched Guides)

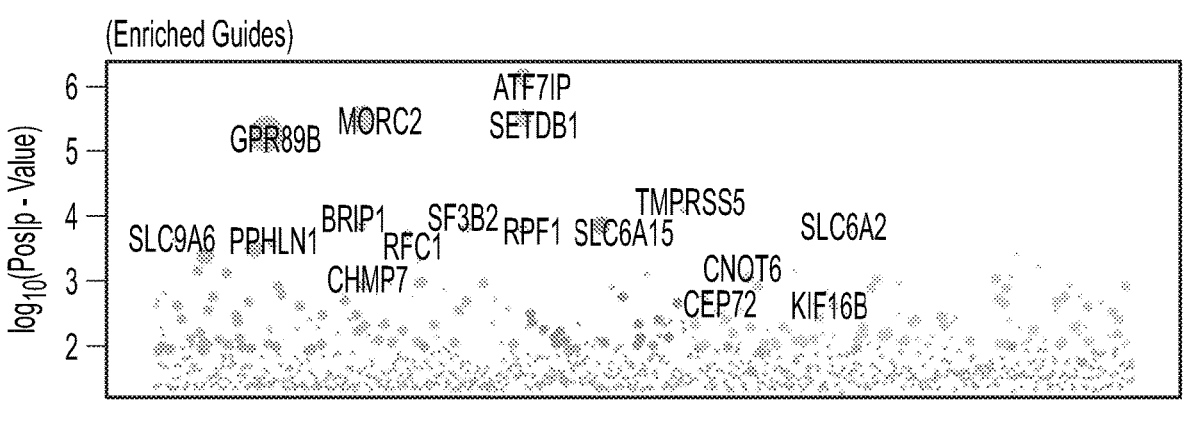

1. Endoplasmic Reticulum or Golgi Associated Genes    4. Glycosphingolipid Metabolic Processing
2. Mitochondrial Genes                                5. Integral Membrane Proteins
3. Nuclear Proteins                                   6. Other sgRNAs

FIG. 2A (Depleted Guides)

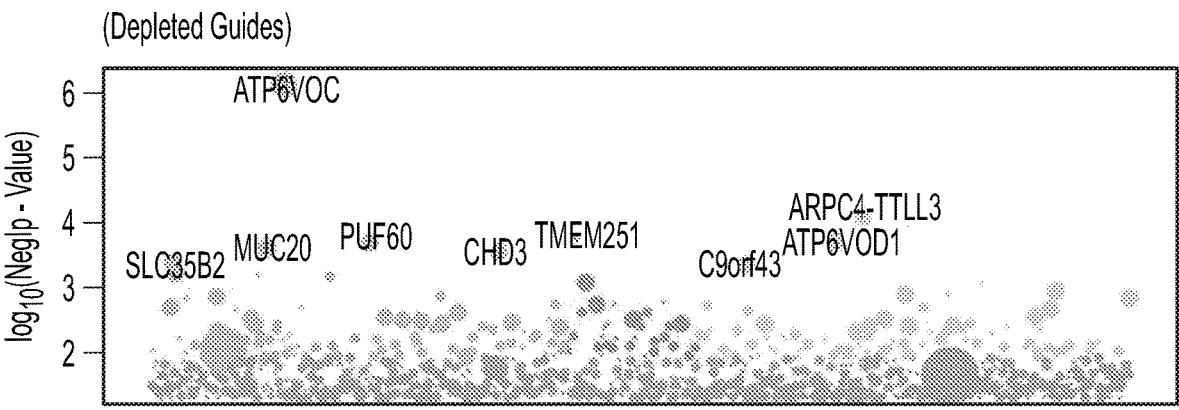

1. Endoplasmic Reticulum or Golgi Associated Genes    4. Glycosphingolipid Metabolic Processing
2. Mitochondrial Genes                                5. Integral Membrane Proteins
3. Nuclear Proteins                                   6. Other sgRNAs

FIG. 2B

Transfections for lysate preparation

Anti-HA

Anti-FLAG

Inputs

SYPRO ruby

IB: B1 (anti VP)

IB: FLAG (AAP)          FIG. 6C

Immunoprecipitations

IP: Anti-HA

SYPRO ruby

IB: B1 (anti VP)          ←VP1

IB: FLAG (AAP)          ←AAP2 (full length)

IP: Anti-FLAG

SYPRO ruby

IB: B1 (anti VP)          ←VP1

IB: FLAG (AAP)          ← AAP2 (full)
                        ⊢[light chain]
                        AAP2C

METHODS AND COMPOSITIONS FOR IMPROVING THE ASSEMBLY OF ADENO-ASSOCIATED VIRUSES (AAVS)

CROSS REFERENCE TO RELATED APPLICATIONS

This application is the National Stage entry of International Patent Application No. PCT/US2020/028015, filed on Apr. 13, 2020, which claims the benefit of priority under 35 U.S.C. § 119(e) to U.S. Application No. 62/833,595 filed on Apr. 12, 2019.

TECHNICAL FIELD

This disclosure generally relates to adeno-associated viruses and methods of producing adeno-associated viruses.

BACKGROUND

Recombinant adeno-associated viruses (rAAV) for use in gene therapy have primarily been produced in mammalian cell lines such as, e.g., 293 cells, COS cells, HeLa cells, KB cells, and other mammalian cell lines (see, e.g., U.S. Pat. Nos. 6,156,303, 5,387,484, 5,741,683, 5,691,176, 5,688, 676, US 20020081721, WO 00/47757, WO 00/24916, and WO 96/17947).

However, in most of these mammalian cell culture systems, the number of rAAV particles generated per cell is on the order of 10E4 particles, and production of rAAV at an even larger scale is required for a clinical study.

Methods of improving the production of rAAV are needed.

SUMMARY

This disclosure provides a number of potential genes and proteins that can be modulated in cultured cells to increase recombinant adeno-associated virus (rAAV) production and/or assembly. The methods described herein can be used to maximize production titers for use in clinical or laboratory applications, including in the field of gene therapy. As described herein, modulation can include knockout, knockdown, or overexpression of select genes in production cell lines, inhibition/activation of select genes by chemical compounds added to culture media, or a combination thereof.

In one aspect, methods for improving the assembly of adeno-associated virus (AAV) in a cell are provided. Such methods typically include: increasing expression or activity of Hsc/Hsp70 or a co-factor thereof, vacuolar-specific H+ ATPase, and/or cyclin-dependent kinase 2 in the cell to produce a modified cell; infecting the modified cell with an AAV vector to produce an infected modified cell; culturing the infected modified cell; and collecting the assembled AAV.

In some embodiments, the amount of assembled AAV collected is greater than the amount of assembled AAV collected following AAV infection of a cell that lacks the modification. In some embodiments, the method results in a significant increase in titer of the AAV.

In another aspect, methods for improving the assembly of adeno-associated virus (AAV) are provided. Such methods typically include: infecting a modified cell with the AAV, wherein the cell has been modified to exhibit an increase or decrease in one or more genes or the protein encoded therefrom selected from CHMP7, CEP72, CNOT6, SLC9A6, PPHLN1, ATF7IP, SETDB1, GPR89B, KIF16B, ATAD3A, BAG2, STUB1, DNAJA1, DNAJC7, HSPA8, HSPA1A, CDK1, CDK2, CHCHD2, C1QBP, DPYSL5, FXR1, FXR2, IPO5, LBR, MTPN, NPM3, NPM1, PPL, SNX3, UBE2O, SAE1, CCDC124, GNB1, RAB1A, GNB4, RPL23, CKB, SRP9, UCHL1, and TBCB; and collecting the assembled AAV.

In some embodiments, the modified cell is a genetically engineered cell. Representative genetically engineered cells include a knockout, a knockdown, over-expression, or combinations thereof.

In some embodiments, the modified cell includes a chemical compound that increases or decreases the one or more genes or the proteins encoded therefrom. Representative chemical compounds include, without limitation, Cdk1 inhibitor IV, Cdk2 inhibitor II, apoptazole, ML-792, BML282, NSC348884, FDNB, and Bafilomycin A1. In still another aspect, cell-free culture systems for assembling adeno-associated virus are provided. Such systems typically include: culture media; and at least two proteins, or nucleic acids encoding the at least two proteins, selected from CHMP7, CEP72, CNOT6, SLC9A6, PPHLN1, ATF7IP, SETDB1, GPR89B, KIF16B, ATAD3A, BAG2, STUB1, DNAJA1, DNAJC7, HSPA8, HSPA1A, CDK1, CDK2, CHCHD2, C1QBP, DPYSL5, FXR1, FXR2, IPO5, LBR, MTPN, NPM3, NPM1, PPL, SNX3, UBE2O, SAE1, CCDC124, GNB1, RAB1A, GNB4, RPL23, CKB, SRP9, UCHL1, and TBCB. In some embodiments, the articles include at least three (e.g., at least four, at least five, etc.) proteins or nucleic acids encoding the at least three (e.g., at least four, at least five, etc.) proteins.

In yet another aspect, cell lines are provided. Such cell lines typically include: one or more mutations in Hsc/Hsp70 or a co-factor thereof, vacuolar-specific H+ ATPase, and/or cyclin-dependent kinase 2; and/or one or more exogenous constructs expressing Hsc/Hsp70 or a co-factor thereof, vacuolar-specific H+ ATPase, and/or cyclin-dependent kinase 2.

In some embodiments, the mutation comprises a knockout mutation. In some embodiments, the mutation comprises a knockdown mutation. In some embodiments, the one or more exogenous constructs includes a recombinant construct.

In another aspect, articles of manufacture for improving the assembly of adeno-associated virus (AAV) in a cell are provided. Such articles typically include at least one member from at least two of (a), (b) or (c): (a) Hsc/Hsp70 or a co-factor thereof, a nucleic acid encoding Hsc/Hsp70 or a co-factor thereof, or a compound that modulates Hsc/Hsp70 or a co-factor thereof; (b) vacuolar-specific H+ ATPase, a nucleic acid encoding vacuolar-specific H+ ATPase, or a compound that modulates vacuolar-specific H+ ATPase; and (c) cyclin-dependent kinase 2, a nucleic acid encoding cyclin-dependent kinase 2, or a compound that modulates cyclin-dependent kinase 2.

In some embodiments, the compound that modulates Hsc/Hsp70 or a co-factor thereof is apoptazole. In some embodiments, the compound that modulates vacuolar-specific H+ ATPase is Bafilomycin A1. In some embodiments, the compound that modulates cyclin-dependent kinase 2 is Cdk2 inhibitor II.

In one aspect, the disclosure features methods for improving the assembly of adeno-associated virus (AAV). Such methods typically include infecting a genetically-engineered cell with the AAV, wherein the cell has been genetically engineered to exhibit an increase or decrease in one or more genes or the encoded proteins selected from CHMP7, CEP72, CNOT6, SLC9A6, PPHLN1, ATF7IP, SETDB1, GPR89B, KIF16B, ATAD3A, BAG2, STUB1, DNAJA1, DNAJC7, HSPA8, HSPA1A, CDK1, CDK2, CHCHD2, C1QBP, DPYSL5, FXR1, FXR2, IPO5, LBR, MTPN, NPM3, NPM1, PPL, SNX3, UBE2O, SAE1, CCDC124, GNB1, RAB1A, GNB4, RPL23, CKB, SRP9, UCHL1, and/or TBCB; and collecting the assembled AAV.

In another aspect, the disclosure features methods for improving the assembly of adeno-associated virus (AAV) in a cell. Such methods typically include infecting the cell with the AAV in the presence of one or more factors selected from Hsc/Hsp70 or a co-factor thereof, vacuolar-specific H+ ATPase, cyclin-dependent kinase 2, and combinations thereof; and collecting the assembled AAV.

In still another aspect, the disclosure features methods for improving the assembly of adeno-associated virus (AAV) in a cell. Such methods typically include modulating one or more factors in a cell, where the factors are selected from Hsc/Hsp70 or a co-factor thereof, vacuolar-specific H+ ATPase, and cyclin-dependent kinase 2; infecting the modulated cell with the AAV; and collecting the assembled AAV.

Generally, following the application of the methods described herein, the amount of assembled AAV collected is greater than the amount of AAV collected following AAV infection of a non-genetically-engineered or modulated cell. Generally, the methods described herein provide an increase in titer of the AAV. Generally, the methods described herein provide for an increase in the quality and performance of the AAV vector preparation.

In some embodiments, the genetic engineering includes one or more of knockout, knockdown, and/or over-expression, or combinations thereof. In some embodiments, modulating is performed using knockout, knockdown, over-expression, or combinations thereof. In some embodiments, modulating is performed using inhibition and/or activation of select genes, e.g., by adding chemical compounds to the culture media.

In yet another aspect, the disclosure provides articles of manufacture for improving the assembly of adeno-associated virus (AAV) in a cell. Such articles of manufacture typically include at least one member from at least two of (a), (b) or (c): (a) Hsc/Hsp70 or a co-factor thereof, a nucleic acid encoding Hsc/Hsp70 or a co-factor thereof, and/or a compound that modulates Hsc/Hsp70 or a co-factor thereof, (b) vacuolar-specific H+ ATPase, a nucleic acid encoding vacuolar-specific H+ ATPase, and/or a compound that modulates vacuolar-specific H+ ATPase; and/or (c) cyclin-dependent kinase 2, a nucleic acid encoding cyclin-dependent kinase 2, and/or a compound that modulates cyclin-dependent kinase 2.

In another aspect, a cell line is provided that includes one or more mutations (e.g., knockout, knockdown) in Hsc/Hsp70 or a co-factor thereof, vacuolar-specific H+ ATPase, and/or cyclin-dependent kinase 2; and/or one or more exogenous (e.g., recombinant) constructs expressing Hsc/Hsp70 or a co-factor thereof, vacuolar-specific H+ ATPase, and/or cyclin-dependent kinase 2.

In another aspect, the disclosure features cell-free culture systems for assembling adeno-associated virus. The systems include culture media; and at least two (e.g., at least three, at least four, at least five, etc.) proteins, or nucleic acids encoding the at least two proteins, selected from CHMP7, CEP72, CNOT6, SLC9A6, PPHLN1, ATF7IP, SETDB1, GPR89B, KIF16B, ATAD3A, BAG2, STUB1, DNAJA1, DNAJC7, HSPA8, HSPA1A, CDK1, CDK2, CHCHD2, C1QBP, DPYSL5, FXR1, FXR2, IPO5, LBR, MTPN,

4

NPM3, NPM1, PPL, SNX3, UBE2O, SAE1, CCDC124, GNB1, RAB1A, GNB4, RPL23, CKB, SRP9, UCHL1, and TBCB.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 2 are plots showing sgRNA abundance at 18 hours post-transfection.

FIGS. 6B and 6C are images of gels that show co-immunoprecipitation from lysates used for anti-HA (VP bait) pulldowns, and anti-FLAG (AAP bait) pulldowns numbered as in FIG. 6A from two replicate experiments, denoted A and B (above lanes). FIG. 6B was stained with SYPRO Ruby to show total protein and FIG. 6C was interrogated for VP and AAP by Western blot.

DETAILED DESCRIPTION

Figure 1:
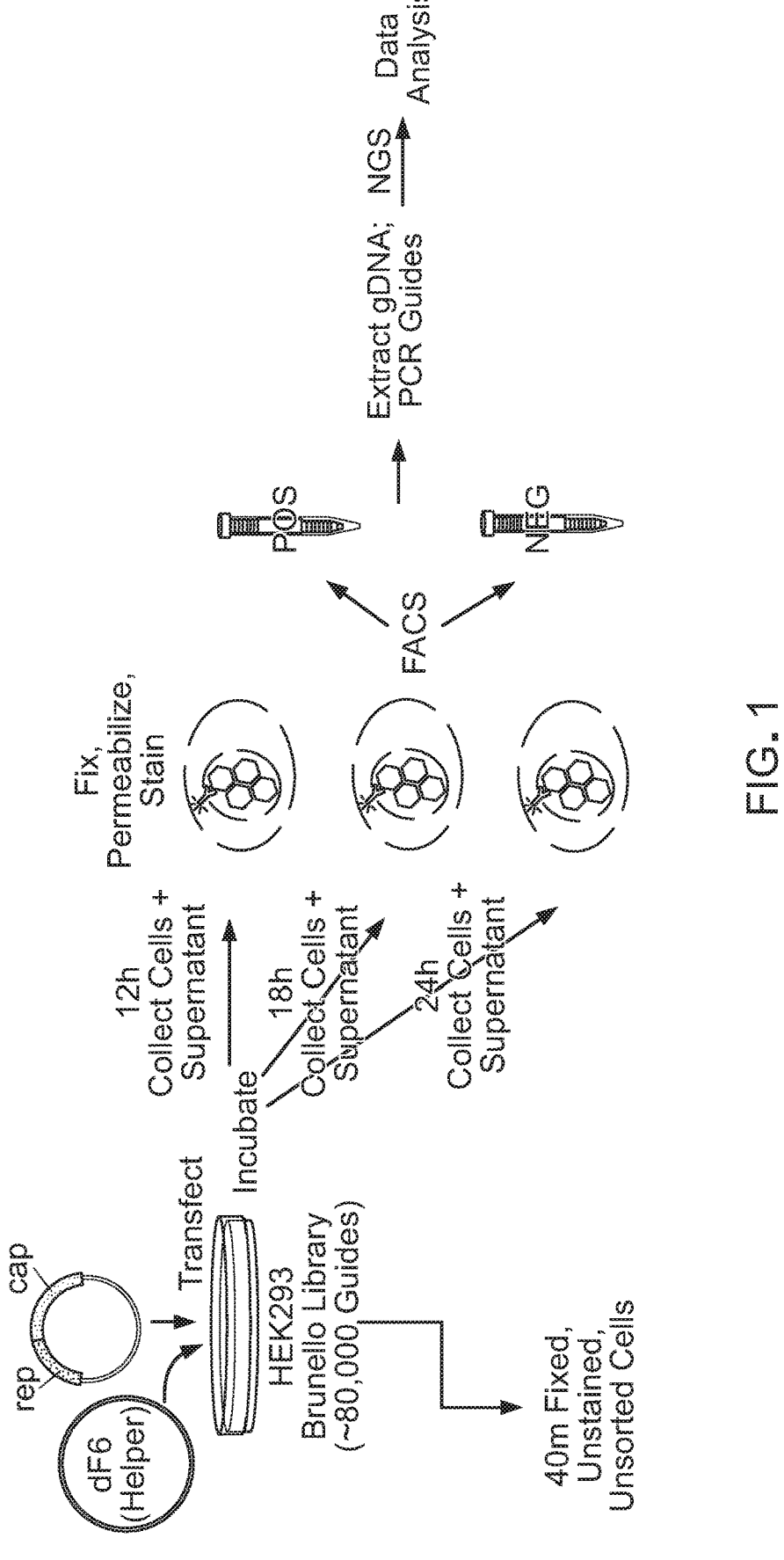
FIG. 1 is a schematic showing the workflow of the CRISPR screen used herein.

We used genomic and proteomic approaches to identify a number of host proteins that are involved in the production and/or assembly of adeno-associated virus (AAV). As described herein, one or more of such proteins, or the nucleic acid encoding one or more of such proteins, can be modified so as to increase the production and/or assembly of AAV in cells. Similarly, one or more of such proteins, or the nucleic acid encoding one or more of such proteins, can be included in a cell-free system to increase the production and/or assembly of AAV. The methods described herein can be used to maximize production titers of viral vectors for use in clinical or laboratory applications, including in the field of gene therapy.

As described herein, methods for improving the assembly of adeno-associated virus (AAV) in a cell typically include increasing expression or activity of Hsc/Hsp70 or a co-factor thereof, vacuolar-specific H+ ATPase, and/or cyclin-dependent kinase 2 in the cell. Once the cell has been so modified, the modified cell can be infected with an AAV vector and subsequently cultured and the assembled AAV collected.

The following host proteins were shown to be involved in the assembly of AAV, and, therefore, any one, or combinations of two or more, of those proteins, or the nucleic acid encoding the protein, can be modified as described herein to improve the production and/or assembly of AAV: charged multivesicular body protein 7 (CHMP7), centrosomal protein 72-kDa (CEP72), CCR4-NOT transcription complex subunit 6 (CNOT6), solute carrier family 9, member 6 (SLC9A6), periphilin 1 (PPHLN1), activating transcription factor 7-interacting protein (ATF7IP), set domain protein bifurcated 1 (SETDB1), G protein-coupled receptor 89B (GPR89B), kinesin family member 16B (KIF16B), ATPase family AAA domain-containing protein 3A (ATAD3A), BAG family molecular chaperone regulator 2 (BAG2), E3 ubiquitin-protein ligase CHIP (STUB1), DnaJ homolog subfamily A member 1 (DNAJA1), DnaJ homolog subfamily C member 7 (DNAJC7), heat-shock 70-kDa protein 8 (HSPA8), heat-shock 70-kDa protein 1A (HSPA1A), cyclin-dependent kinase 1 (CDK1), cyclin-dependent kinase 2 (CDK2), coiled-coil-helix-coiled-coil-helix domain-containing protein 2 (CHCHD2), complement component 1Q subcomponent-binding protein (mitochondrial) (C1QBP), dihydropyrimidinase-related protein 5 (DPYSL5), fragile X mental retardation syndrome-related protein 1 (FXR1), fragile X mental retardation syndrome-related protein 2 (FXR2), importin-5 (IPO5), lamin-B receptor (LBR), myotrophin (MTPN), nucleoplasmin-3 (NPM3), nucleophosmin (NPM1), periplakin (PPL), sorting nexin-3 (SNX3), E3-in-dependent E2 ubiquitin-conjugating enzyme (UBE2O), SUMO-activating enzyme subunit 1 (SAE1), coiled-coil domain-containing protein 124 (CCDC124), guanine nucleotide-binding protein G(I)/G(S)/G(T) subunit beta-1 (GNB1), Ras-related protein Rab-1A (RAB1A), guanine nucleotide-binding protein subunit beta-4 (GNB4), 60S ribosomal protein L23 (RPL23), creatine kinase B-type (CKB), signal recognition particle 9 kDa protein (SRP9), ubiquitin carboxyl-terminal hydrolase isozyme L1 (UCHL1), and/or tubulin-folding co-factor B (TBCB).

As described herein, modifying a host cell to increase expression or activity of Hsc/Hsp70 or a co-factor of the Hsc/Hsp70 pathway that participate in VP folding (e.g., Bag2, STUB1, DnaJC7, or DnaJA1), vacuolar-specific H+ ATPase and/or cyclin-dependent kinase 2 can improve (or increase) the production and/or assembly of AAV in that host cell.

As described herein, the terms "modify" or "modified" are understood to include any type of manipulation of the cell that results in an increase or a decrease in expression or activity of one or more of the host proteins described herein. Therefore, as used herein, modifying cells can include, without limitation, knocking-out or knocking-down the expression of an endogenous nucleic acid sequence (using, e.g., mutagenesis) or over-expressing an exogenous nucleic acid sequence (e.g., a construct or a vector containing a recombinant nucleic acid molecule). Modifying cells also can include, without limitation, exposing the cells to one or more chemical compounds (e.g., in the culture media) to either increase or inhibit the activity, directly or indirectly, of one or more of the endogenous host proteins described herein.

Representative chemical compounds that can be used to increase or decrease the one or more genes or the proteins encoded therefrom. Representative chemical compounds include, without limitation, Cdk1 inhibitor IV, Cdk2 inhibitor II, apoptazole, ML-792, BML282, NSC348884, FDNB, and Bafilomycin A1.

Methods of increasing the expression or activity of a protein are known. For example, the nucleic acid encoding the protein can be over-expressed in the host cell. Nucleic acid constructs for over-expressing a nucleic acid are known in the art and are commercially available. It would also be appreciated that expression or activity of a protein can be stimulated using a chemical compound, and methods of screening for compounds that exhibit such activity are known in the art.

Methods of decreasing the expression or activity of a protein are known. For example, the nucleic acid encoding the protein can be mutated so as to knockout or knockdown the expression or the activity of the protein. Methods of mutagenesis are known in the art and generally are performed using the polymerase chain reaction (PCR). It would also be appreciated that expression or activity of a protein can be inhibited using a chemical compound, and methods of screening for compounds that exhibit such activity are known in the art.

In addition, cell lines are provided that include one or more mutations in Hsc/Hsp70 or a co-factor thereof, vacuolar-specific H+ ATPase, and/or cyclin-dependent kinase 2; and/or one or more exogenous constructs expressing Hsc/Hsp70 or a co-factor thereof, vacuolar-specific H+ ATPase, and/or cyclin-dependent kinase 2.

Once a cell has been modified as described herein, the modified cell can be used to produce one or more AAV vectors under appropriate conditions. An AAV vector (e.g., a vector encoding the minimal viral proteins required to produce and assemble an AAV particle) can be a wild type AAV or a recombinant AAV (rAAV). Methods of production of AAV and appropriately culturing these mammalian cells are well known in the art and include methods of transfection of the required AAV components, use of cell lines stably expressing the AAV production components, and/or use of heterologous viral vector systems such as Herpes Simplex Virus or Adenovirus to infect cell to delivery AAV components to the cell as described in Sandoval et al., 2019, Viral Vectors for Gene Therapy.

The modification of the host proteins, or the nucleic acids encoding such host proteins, can result in improved assembly of AAV. Improved assembly of AAV refers to an increase in the number of assembled AAV or an increase in the rate or efficiency of assembly relative to AAV assembled in the absence of the modification. The methods described herein result in an increase (e.g., a significant increase) in the titer of the resultant AAV. In some instances, the methods described herein increase the quality and performance of the AAV (e.g., higher yield, increased viability, and/or improved infectivity) relative to an AAV produced in the absence of the modification.

The proteins identified herein, or the nucleic acids encoding such proteins, can be used in the development of cell-free AAV production methods. For example, a cell-free system can be designed and used to generate AAV particles in the absence of an actual cell. Such a cell-free system can include, for example, nucleic acids encoding one or more (e.g., at least one, at least two, at least three, at least four, at least five, at least six) of such proteins or the proteins themselves. For example, one or more of the following proteins, or the nucleic acid encoding one or more proteins, can be provided in a cell-free system: CHMP7, CEP72, CNOT6, SLC9A6, PPHLN1, ATF7IP, SETDB1, GPR89B, KIF16B, ATAD3A, BAG2, STUB1, DNAJA1, DNAJC7, HSPA8, HSPA1A, CDK1, CDK2, CHCHD2, C1QBP, DPYSL5, FXR1, FXR2, IPO5, LBR, MTPN, NPM3, NPM1, PPL, SNX3, UBE2O, SAE1, CCDC124, GNB1, RAB1A, GNB4, RPL23, CKB, SRP9, UCHL1, and/or TBCB.

The amount of assembled AAV collected following use of the methods described herein is typically greater (e.g., significantly greater) than the amount of assembled AAV collected following AAV infection of a cell that lacks the modification. In some instances, the methods described herein result in a significant increase in titer of the AAV.

Articles of manufacture for improving the assembly of adeno-associated virus (AAV) in a cell also are provided. Such articles typically include at least one member from at least two of (a), (b) or (c): (a) Hsc/Hsp70 or a co-factor thereof, a nucleic acid encoding Hsc/Hsp70 or a co-factor thereof, or a compound that modulates Hsc/Hsp70 or a co-factor thereof; (b) vacuolar-specific H+ ATPase, a nucleic acid encoding vacuolar-specific H+ ATPase, or a compound that modulates vacuolar-specific H+ ATPase; and (c) cyclin-dependent kinase 2, a nucleic acid encoding cyclin-dependent kinase 2, or a compound that modulates cyclin-dependent kinase 2.

A representative compound that modulates Hsc/Hsp70 or a co-factor thereof is apoptazole; a representative compound that modulates vacuolar-specific H+ ATPase is Bafilomycin A1; and a representative compound that modulates cyclin-dependent kinase 2 is Cdk2 inhibitor II.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Screening for Factors Associated with Optimal AAV Assembly

Briefly, two different screening approaches were performed to identify factors in HEK293 cells that play a role in AAV assembly and/or packaging of DNA. These two properties combined constitute manufacturing, and the modulation of one or more of these factors can enhance the manufacturing yields of AAVs. The two screening approaches were designed as follows.

Co-Immunoprecipitation and Mass Spectrometry

Various viral proteins known to be involved in assembly were protein tagged and, following a HEK293 transfection, a co-immunoprecipitation was performed. The proteins that were pulled down in the complex were analyzed via mass spectrometry. The most trustworthy hits were reported based on the co-IP of these proteins with various viral components, their biology, and their unlikeliness of being background (based, for example, on controls and control mass spectrometry data sets). This method primarily screened for proteins involved in some aspect of the assembly of the particle (e.g., the coming together of the protein particles) and the cellular co-factors associated with these assembly proteins.

Sample Preparation

Samples were prepared as described previously (Maurer et al., 2019, J. Virol., 93:93(7): doi: 10.1128/JVI.02013-18), omitting the blocking step and detergent in the wash steps, as these reagents are incompatible with LC-MS/MS and downstream analysis.

Peptide Digestion

After immunoprecipitation, the proteins bound to beads were frozen at −80° C. in 50 uL of 50 mM Tris. The samples were thawed and a solution of urea, dithiothreitol (DTT, Thermo Scientific, 20291), trypsin (Promega, V511X), and Tris was added such that the beads for each of the 20 samples were suspended in 80 uL of 2M urea, 50 mM Tris HCL (pH 8), 5 ug/mL trypsin, and 5 mM DTT. Samples were incubated for 1 hour, shaking at 25° C. Supernatant was transferred to a new tube and the beads were washed twice with 60 uL of 5.33 M urea, 50 mM Tris HCL solution, and the wash buffer was combined with supernatant for each sample. The solution was centrifuged at 5000 rcf for 2 minutes and then transferred to a new tube. Proteins were reduced with 4 mM DTT for 30 minutes at 25° C. and then alkylated with 10 mM iodoacetamide (Sigma, A3221) for 45 minutes in the dark at 25° C. Afterwards, 0.5 ug to trypsin was added to each sample and the samples were digested overnight at 25° C. with shaking. The digests were quenched with 1% formic acid (FA; Fluka, 56302). Samples were desalted using stage tips containing 2 Empore C18 punches (3M, 2315). All spins were performed at 1,500 rcf for 2 minutes. Stage tips were conditioned with 1×50 uL 50% acetonitrile (ACN)/0.1% FA and 2×50 uL 0.1% FA. Samples then were loaded onto stage tips and spun through. Afterwards, samples were washed with 2×50 uL 0.1% FA and eluted off the stage tip with 1×50 uL 50% ACN/0.1% FA and dried down.

TMT Labeling and Strong Cation Exchange Fractionation

For TMT labeling, each sample was reconstituted in 100 uL 50 mM HEPES. 0.8 mg of TMT10 Isobaric Mass Tag (Thermo Fisher) in 41 uL 100% ACN then was added to each sample. Samples were labeled for 1 hour at 25° C. Labeling efficiency was checked to ensure proper and complete labeling. In addition, a mixing control was performed for each TMT 10-plex of samples to ensure 1:1 mixing of all samples. The labeling reaction was quenched with 8 uL 5% hydroxylamine for 15 minutes at 25° C. Afterwards, the samples for each respective 10-plex were mixed together in amounts to provide a 1:1 ratio between all samples and dried down. Each 10-plex sample was resuspended in 1 mL of 0.1% FA and desalted using a Sep-Pak C18 columns (Waters, 100 mg WAT023590). Columns were conditioned with 1×1 mL 100% ACN, 1×1 mL 50% ACN/0.1% FA, and 4×1 mL 0.1% triflouroacetic acid (TFA). Each sample was loaded onto a column and washed with 3×1 mL 0.1% TFA and 1×1 mL 1% FA. Peptides were eluted off the column with 2×0.6 mL 50% ACN/0.1% FA and dried down.

The samples were reconstituted in 200 uL of 3% ACN/0.1% FA. Half of each sample was taken and dried down to be analyzed using HPLC-HCD-MS/MS. The other half was dried down and resuspended in 250 uL of 0.5% acetic acid (AcOH) to be fractionated using strong cation exchange. Samples were fractionated using stage tips with 3 SCX punches at the bottom (3M, 2251) and 2 C18 punches on top. All spins were performed at 3,500 rcf for 2 minutes. Stage tips were conditioned with 1×100 uL methanol (MeOH), 1×100 uL 80% ACN/0.5% AcOH, 1×100 uL 0.5% AcOH, 1×100 uL 20% ACN/0.5% AcOH/500 mM NH4AcO, and 1×0.5% AcOH. Samples were loaded and spun through. The stage tip was washed with 2×100 uL 0.5% AcOH. The peptides were trans-eluted from the C18 to the SCX punches with 1×100 uL 80% ACN/0.5% AcOH. Peptides then were eluted off the stage tip into 3 fractions with 1×50 uL 20% ACN/50 mM NH4AcO (pH 5.15), 1×50 uL 20% ACN/50 mM NH4HCO$_3$ (pH 8.25), and 1×50 uL 20% ACN/0.1% NH4AcO (pH 10.3). Each eluted fraction was then diluted with 200 uL of 0.5% AcOH and desalted using a 2 punch C18 stage tip. Stage tips were conditioned with 1×100 uL MeOH, 1×100 uL 80% ACN/0.5% AcOH, 2×100 uL 0.5% AcOH. Samples were loaded and spun through. Afterwards, stage tips were washed with 2×100 uL 0.5% AcOH. Samples were eluted off the stage tip with 60 uL 80% ACN/0.5% AcOH. Each fraction was dried down and resuspended in 9 uL 3% ACN/0.1% FA for LC-MS-MS analysis. The unfractionated half of the sample was also resuspended in 9 uL 3% ACN/0.1% FA for LC-MS-MS analysis.

LC-MS/MS and Spectra Analysis

All samples were analyzed using nanoflow HPLC-HCD-MS/MS with an Orbitrap Fusion Lumos mass spectrometer and an Easy-nLC 1200 system. 4 uL of each sample was injected at a flow rate of 500 nl/min onto a Picofrit column self-packed with 1.9 um C-18 beads that was heated to 50° C. The LC-MS/MS gradient and flow rate were used as previously described (Mertins et al., 2016, Nature, 534:55-62). Spectra were acquired for 110 minutes. MS1 scans were acquired at 60k resolution at a scan range of 350-1800 m/z and a maximum injection time of 50 ms. Ions were fragmented with a collision energy of 38%. MS2 scans were acquired at 50k resolution with a maximum injection time of 105 ms in a 0.7 isolation window.

Data were searched with Spectrum Mill (Agilent) using the Uniprot Human database, in which the viral proteins were appended. A fixed modification of carbamidomethylation of cysteine and variable modifications of N-terminal protein acetylation, oxidation of methionine, and TMT 10 plex labels were searched. The enzyme specificity was set to LysC/trypsin and a maximum of three missed cleavages was used for searching. The maximum precursor ion charge state was set to 6. The precursor and product ion mass tolerances were set to 20 ppm. The peptide and protein false discovery rates were calculated to be less than 1%. All non-human proteins and human proteins identified with only one peptide spectral match were excluded from downstream analyses. The moderated T-test (see software.broadinstitute.org/cancer/software/genepattern/on the World Wide Web) was used to determine proteins statistically enriched in each individual experiment. After correcting for multiple comparisons (Benjamin-Hochberg procedure), any proteins with an adjusted p-value of less than 0.05 were considered statistically enriched. Enriched proteins were normalized to the amount of bait protein in each individual experiment by subtracting the log 2 fold enrichment value of the bait from each enriched protein value. The data were grouped to visualize the mean relative enrichment across the four experimental conditions using software.broadinstitute.org/morpheus/on the World Wide Web).

Use of CRISPR/Cas9

AAV was produced in HEK293 cells that expressed CRISPR/Cas9 and that had been transfected with a gRNA library containing gRNAs for all known human genes. AAV-producing cells were selected by FACS sorting using an anti-AAV antibody that only detects an assembled capsid protein (i.e., not the monomer). gRNAs that were enriched in the selected cells indicated that the gRNA target, when knocked out, improved AAV production. The most statistically significant hits are reported based on (a) the significance of the enrichment over control, (b) the number of gRNAs for the same gene that demonstrated this effect (these libraries are redundant in that they often have 6 gRNAs per target gene), and (c) the biology of the genes/protein hits in possible relation to AAV assembly/packaging. This method interrogates both assembly and packaging (e.g., the loading of viral DNA into a preformed particle).

FIG. 1 is a schematic of the CRISPR screen pipeline. HEK293 cells were transduced at a MOI of <1 with the Brunello library, a lentiviral Cas9+sgRNA library with an average of 4 guides targeting each protein coding gene. Untransduced cells were removed by antibiotic selection, and the resulting knock-out cell library was cultured and expanded. Cells were transfected with Adenoviral Helper (dF6) and rep2-cap8 AAV production plasmids. Approximately 800 million cells were collected at each of three time points (12 h, 18 h, and 24 h). Cells were gently fixed and permeabilized (to allow the capsid antibodies to reach the nucleus), then stained with the ADK8 monoclonal antibody, which recognizes a conformational epitope only present in assembled capsids, followed by the addition of a secondary fluorescent antibody. The stained cells were FACS sorted to separate productive cells (POS, containing capsids) from non-productive cells (NEG). Genomic DNA was then extracted and integrated guide sequences were PCR amplified and Illumina sequenced.

Next Generation Sequencing Data Analysis

Differentially enriched sgRNAs were determined through the MAGeCK software package, version 0.5.7 (Li et al., 2014, Genome Biology, 15:554). Briefly, sgRNAs were sequenced, mapped and quantified (Sanson et al., 2018, Nat. Commun., 9:5416) before being normalized to reads per million according to the formula: reads per sgRNA/total reads per condition*10$^6$. To control for the effect of sorting on sgRNA abundances, sgRNA abundances from positive cells were compared with those from negative cells from the same sort. Differential enrichment of sgRNAs at the gene-level was then determined by Robust Ranking Aggregation (RRA) as implemented in MAGeCK.

Visualization of NGS Analysis

The results of the statistical analysis regarding differential enrichment of sgRNAs were visualized through the Matplotlib visualization library (Hunter, 2007, Comp. Science & Eng., 9:90-95) as implemented in Python. To visualize relationships among genes, genes classified into gene ontology terms (Ashburner et al., 2000, Nat. Genet., 25:25-29; The Gene Ontology C., 2017, Nuc. Acids Res., 45:D331-8; Carbon et al., 2009, Bioinform., 25:288-9), listed in Table 1. All lists of human genes associated with the above Gene Ontology terms were accessed by Amigo2.5.2 and downloaded on Sep. 13, 2018.

The top 1000 genes (ranked by significance of enrichment) were then plotted as dots according to their multiple-tests uncorrected p-value along the y-axis and were randomly scattered within their categories along the x-axis. The size of the dots in the plot vary according to the formula $5 \times Ne3$, where N is the number of sgRNAs determine to be differentially enriched by upstream analysis.

TABLE 1

| Gene Ontology Terms | |
| --- | --- |
| Label in Publication | Gene Ontology Term Number(s) |
| Endoplasmic Reticulum or Golgi Apparatus Genes | GO:0005794, GO:0005783 |
| Integral Components of Membrane | GO:0016021 |
| Mitochondrial Genes | GO:0005739 |
| Nuclear Genes | GO:0005634 |
| Glycosphingolipid Metabolic Processing | GO:0006687 |

Example 2—Identification of Assembly and Restriction Factors from the Genome-Wide Screen With the ultimate goal of creating a cell line or culture conditions that would maximize either the number of cells producing vector, the amount of vector produced by each cell, or both, productive cells from a pooled library of cells representing genome-wide perturbations were selected. The CRISPR knockout Brunello library (Doench et al., 2016, Nat. Biotechnol., 34:184-91) was chosen for initial screening, with the intention to repeat the screen with a CRISPRa library. While AAV2 is the most studied serotype, it is the only serotype to demonstrate strictly nucleolar assembly, among other unique phenotypes. AAV8 was chosen to maximize the chances of novel findings, but moreover, AAV8 is phylogenetically more proximal to a larger number of natural variants, which increases the likelihood that these findings will be broadly applicable toward production of many serotypes. The experimental workflow is diagrammed in FIG. 1, and the guide sequences, therefore, serve as the readout for gene knockouts that correlate with productive cells.

In practice, cells that stain positive with capsid specific antibodies were not observed earlier than 12 hours after transfection. At the 12 h time point, less than 1% of the population stained capsid positive. No genes were found to be statistically enriched in the 12 h positive population compared to an unsorted population. The 18 h and 24 h samples stained 6.25% and 6.29% positive, respectively, and the analysis of the guide sequences enriched or depleted in these samples are presented in FIGS. 2 and 3.

The top 1000 genes, ranked by significance of enrichment or depletion in the positive sorted population at 18 h (FIG. 2) and 24 h (FIG. 3) post-transfection compared to the negative population, were plotted as dots according to their multiple-tests uncorrected p-value along the y-axis and randomly scattered within their Gene Ontology categories (color coded and listed below plots) along the x-axis. The size of the dots in the plot vary according to the formula $5 \times Ne3$, where N is the number of sgRNAs determined to be differentially enriched by upstream analysis.

Figure 3A:
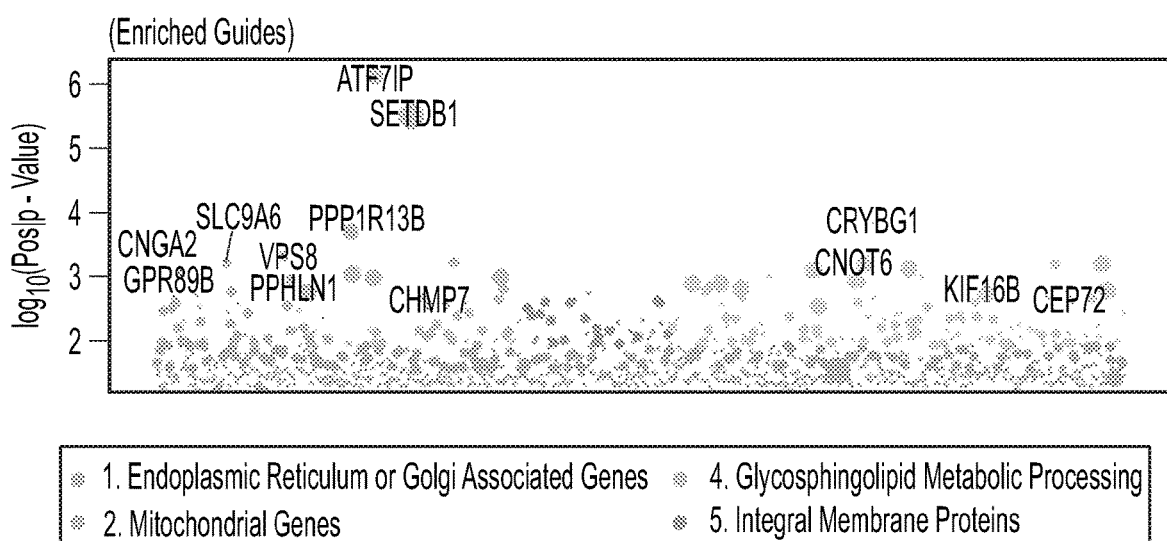
FIG. 3 are plots showing sgRNA abundance at 24 hours post-transfection.
Figure 3B:
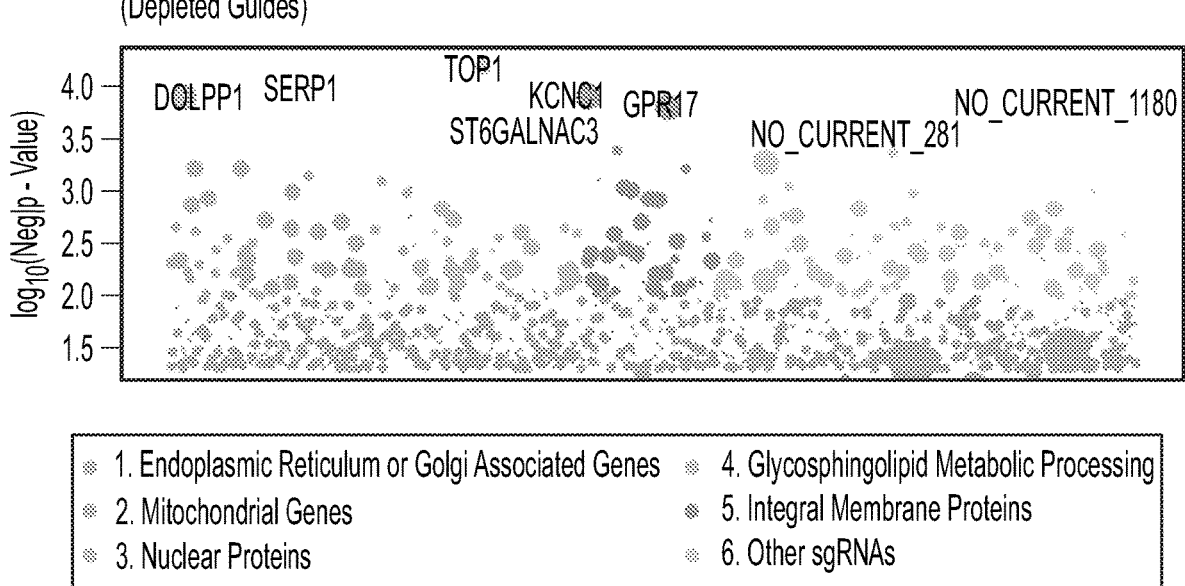

There were several statistically significant guides that were unique to only one time point (18 h or 24 h), but a set of 9 statistically significant guides overlapped in both sets (in bold font in FIGS. 2 and 3). Two genes, ATF7IP and SETDB1, demonstrated particularly high significance in both samples.

To further examine the genes, siRNA knockdown was selected due to the ease with which HEK293 cells are transfected and the time, labor, and cost advantage of siRNA over generating stable cell lines with genetic perturbations. A subset of nine highly ranked genes enriched in both the 18h and 24h samples were chosen, since their appearance in the top 65 hits in both samples suggests a higher likelihood to functionally validate (bold type in FIGS. 2 and 3).

Figure 4:
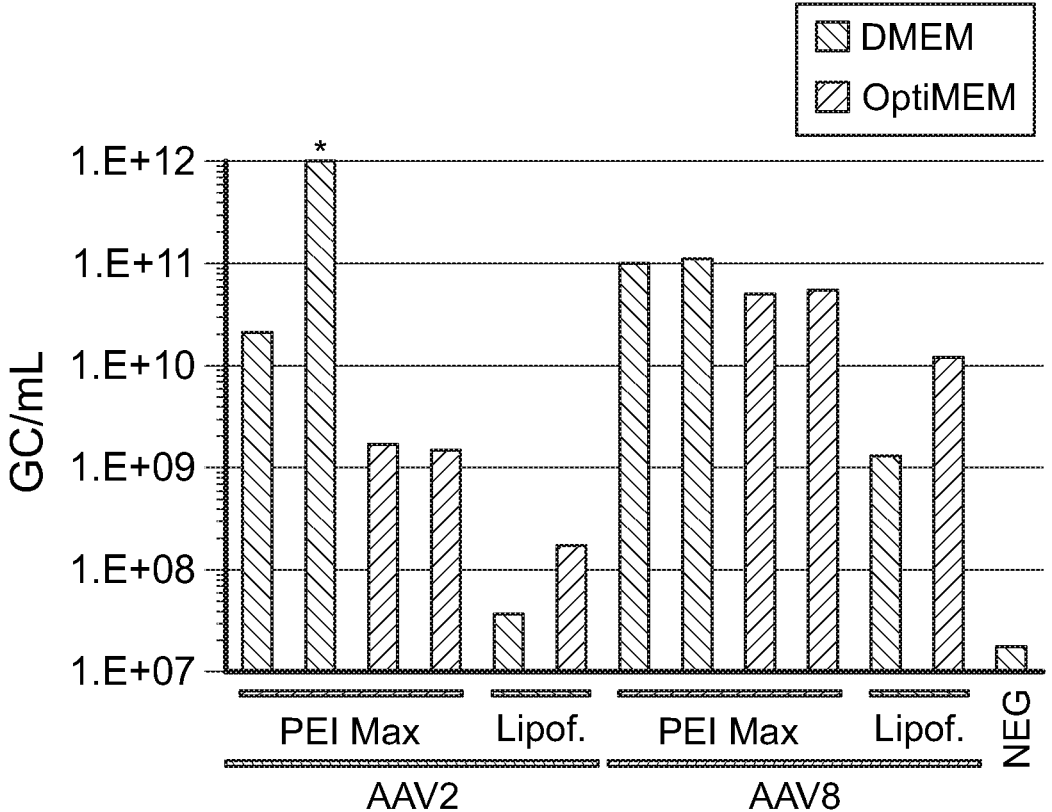
FIG. 4 is a graph showing the effect of transfection methods on vector titer. The graph represents a single experiment; *determined to be contaminated.

In preparation for siRNA transfections, transfection reagents and media other than PEI and serum-free DMEM were examined for their effect on vector production. Lipofectamine and OptiMEM, known to have high transfection efficiency and commonly used for transfection of small nucleic acids, were tested in parallel and in all permutations with PEI and DMEM (FIG. 4). Cells were grown in 6-well plates in DMEM+10% FBS to 90% confluency before transfection. Identical plasmid quantities were used in each condition, with AAV2/2 or AAV2/8 rep/cap plasmids or empty plasmid (NEG) as indicated on x-axis.

The µg transfection reagent: µg DNA ratio was maintained at 1.375:1 across all conditions (x-axis, PEI Max and Lipofectamine). Transfection mixtures were prepared in 100 µL serum-free DMEM (dark bars) or 100 µL OptiMEM (light bars). After incubation, transfection mixtures were added to cells by one of two methods: (a) culture media was aspirated from well, 1.9 mL of appropriate media was added to transfection mixture, mixed, and added to well (solid bars), or (b) culture media was aspirated from well and replaced with 1.9 mL of appropriate media, then transfection mixture was added dropwise on top of media in each well (patterned bars). The NEG condition used PEI Max with the mixing method. Crude vector preps were harvested after 48 h and DRPs quantified by qPCR. One of the samples was determined to be contaminated (indicated by an asterisk).

Despite initial transfection efficiencies being far superior with Lipofectamine, as assessed visually by the number and intensity of GFP positive cells, AAV2 and AAV8 vector titer was significantly lower when Lipofectamine was used-100-fold or more in several cases. PEI was preferred for vector production because of its significantly lower cost, but the findings described herein suggest that Lipofectamine based transfections have an inhibitory effect on production. Considering these negative effects, PEI was used for the siRNA experiments despite the lower transfection efficiency.

siRNA targeting the subset of overlapping top genes were transfected 24 h prior to transfection with vector production plasmids to allow knockdown to take effect before production began. Production plasmids and siRNA were then transfected together, and crude preps were harvested and titrated 48 hours after the second transfection (FIG. 5). Briefly, SmartPOOL siRNAs targeting the genes listed on the x-axis were transfected into HEK293 cells using the drip method along with DMEM+5% FBS. After 24 h, cells were transfected again with the siRNAs, adding helper, rep-cap, and ITR.cmv.EGFP.T2A.luciferase.ITR plasmids. Crude vector preparations were harvested 48 h later.

Figures 5A, 5B:
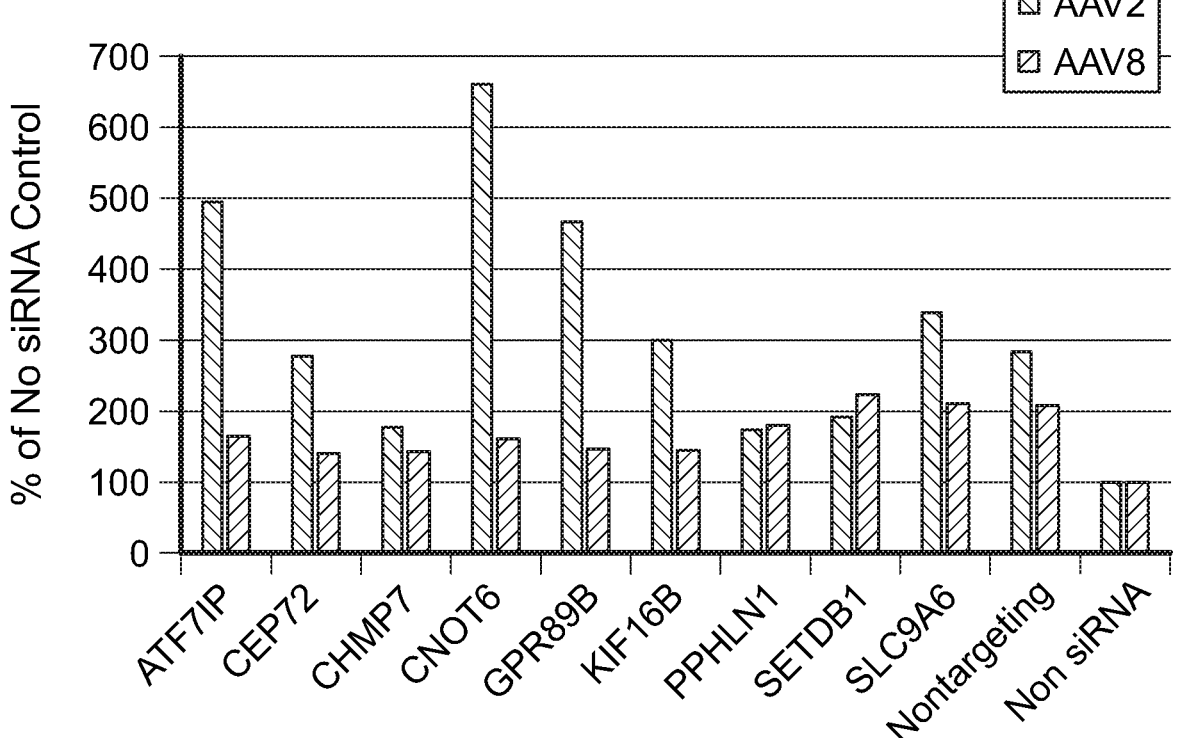
FIG. 5A is a graph showing the effect of siRNA pre- and co-transfection on vector production as a percentage of a parallel transfection using siRNA that does not target any sequence in the human genome. Represents the average of duplicate experiments.
FIG. 5B is a graph showing the effect of siRNA pre- and co-transfection on vector production as a percentage of a parallel mock transfection. Represents the average of duplicate experiments.

DRPs were quantified by qPCR and are reported two ways: as a percentage of a parallel transfection using siRNA that does not target any sequence in the human genome (FIG. 5A), and as a percentage of a parallel mock transfection (FIG. 5B). As controls, one parallel well was transfected with non-targeting siRNA to control for effects of siRNA pre-and co-transfection, and one well was not transfected with any siRNAs (i.e., only production plasmids).

Reporting titers of AAV2 and AAV8 crude preps as a percentage of the non-targeting siRNA control titers (FIG. 5A), there was no appreciable increase in vector titer seen with knockdown of any of the genes of interest. However, when reported as a percentage of the no siRNA control (FIG. 5B), AAV2 but not AAV8 showed an appreciable increase in titer, as much as 6.5-fold with CNOT6 knockdown. Perhaps the most interesting observation was that even the non-targeting siRNA caused a small increase in vector titer, suggesting that activation of the RNAi pathways somehow enhanced production.

Example 3—Virus-Host Protein-Protein Interactions in the Context of Assembly To gain a mechanistic understanding of the assembly process and of the machinery that is directly involved, host factors that physically interact with AAP and capsid monomers before and during their assembly into the icosahedron were identified. It previously was shown that immunoprecipitation of VP-VP-AAP complexes by an HA-tagged VP1 as bait does not precipitate fully assembled capsids (Maurer et al., 2018, Cell Resp., 23:1817-30). Additionally, AAP is not thought to be part of the assembled capsid, but if it is, it is likely on the interior and would thus be inaccessible to antibodies for co-precipitation. Therefore, it was reasoned that proteins co-precipitated by FLAG-AAP or HA-VP1 represent interactions that occur before or during capsid assembly. To maximize the potential mechanistic insight, pulldowns were designed to probe many different interactions (FIG. 6).

Figure 6A:
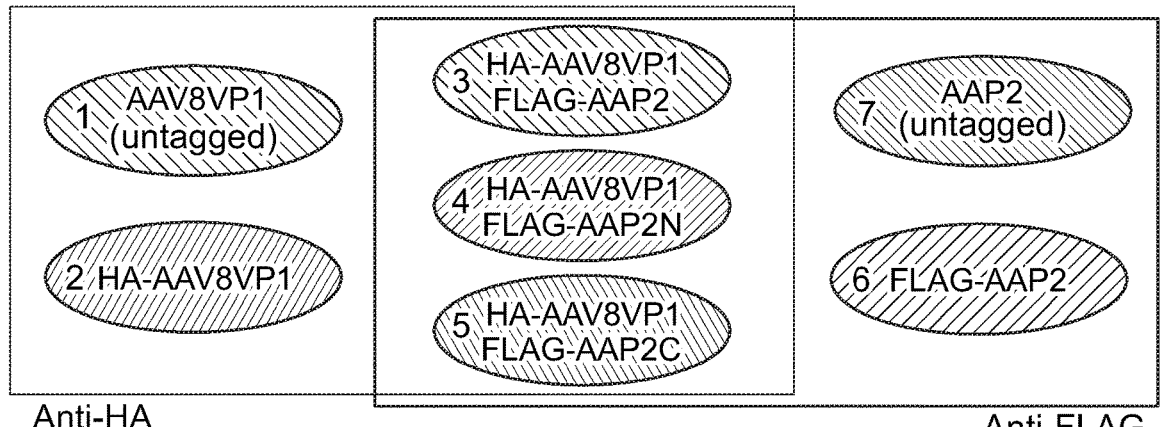
FIG. 6A is a schematic of HEK293 cells transfected with the expression constructs shown within the numbered ovals.
Figure 6B:
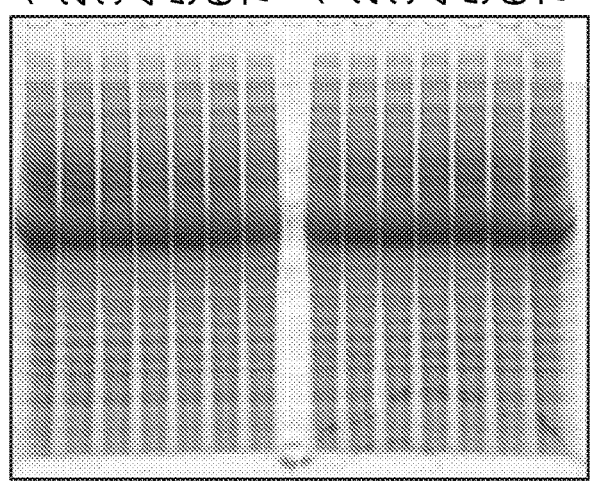
Figure 6D:
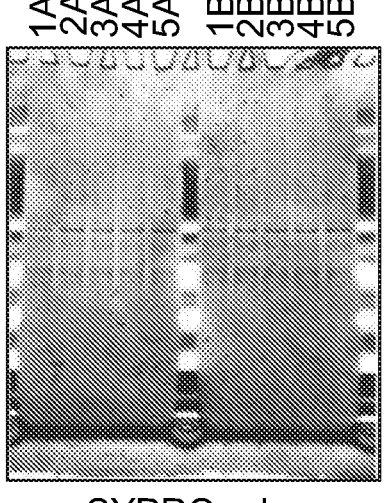
FIG. 6D-6G are gels that show immunoprecipitations performed on equal volumes of lysates prepared as in FIG. 6A. Equal volumes of eluate were loaded per lane and electrophoresed and either stained by SYPRO Ruby to show total protein (FIGS. 6D & 6F) or interrogated for VP and AAP by Western blot (FIGS. 6E & 6G).
Figure 6E:
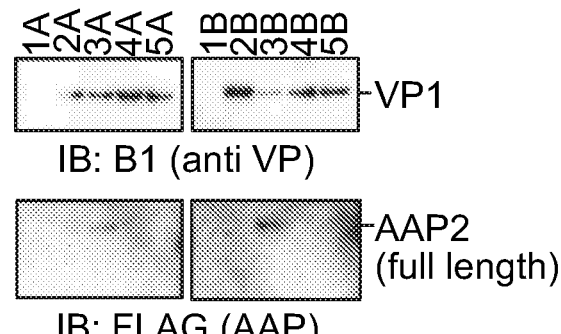
Figure 6F:
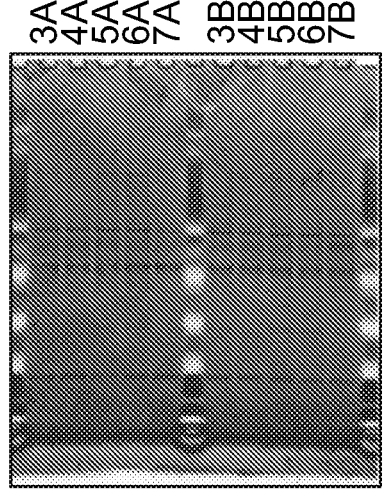
Figure 6G:
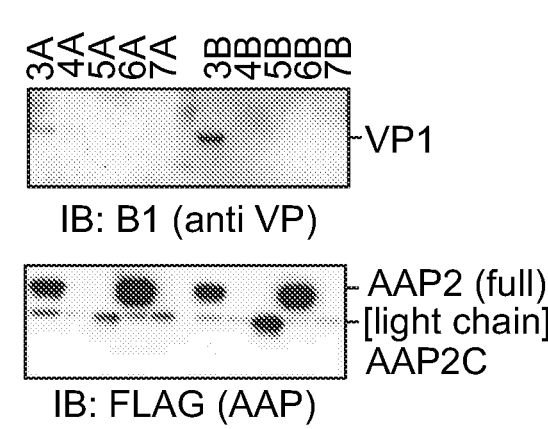

Briefly, HEK293 cells were transfected with the indicated expression constructs FIG. 6A. Cell lysates were prepared and total protein measured by BCA, then diluted accordingly to equalize total protein concentration across samples. The boxes indicate lysates used for anti-HA (VP bait) pulldowns (FIG. 6B) and anti-FLAG (AAP bait) pulldowns (FIG. 6C). 2% of each input lysate (numbered as in FIG. 6A) from two replicate experiments (denoted "A" and "B" above the lanes) was electrophoresed and stained with SYPRO Ruby to show total protein (FIG. 6B) or interrogated for VP and AAP by Western blot (FIG. 6C). Immunoprecipitations then were performed on equal volumes of lysates (described in FIG. 6A). Equal volumes of eluate were loaded in each lane and electrophoresed, and stained by SYPRO Ruby to show total protein (FIGS. 6D and 6F) or interrogated for VP and AAP by Western blot (FIGS. 6E and 6G).

These experiments allowed for the interrogation of cellular proteins that bind VP monomers (Sample 2), those that bind AAP (Sample 6), and those that bind VP-AAP complexes or VP oligomers (Sample 3). In addition, these experiments allowed for examination of how VP interaction partners change in the presence or absence of AAP and vice versa (comparing Sample 2 or 6 with Sample 3).

The N terminal third of AAP (AAPN) encompasses the hydrophobic region and the conserved core, and has been shown to be critical for AAP to function with VP (Maurer et al., 2018, supra; Tse et al., 2018, J. Virol., 92(14):doi:10., 1128/JVI.00393-18), and the C-terminal portion of AAP (AAPC) harbors the nucleolar and nuclear localization signals (Earley et al., 2015, J. Virol., 89:3038-48). We speculated, therefore, that cellular proteins responsible for nuclear translocation of AAP and, by extension, VP, bind AAPC, and that AAPN is primarily responsible for binding VP directly. To test this, FLAG-tagged truncated versions of AAP (AAPN and AAPC) were included in the transfections and pulldowns (FIG. 6, Samples 4 and 5, respectively). Co-immunoprecipitations were performed in both directions, using HA-VP1 or FLAG-AAP as bait, and untagged versions of VP and AAP were expressed in control samples on which anti-HA and anti-FLAG pulldowns were performed to assess nonspecific binding proteins (Samples 1 and 7), which would be subtracted from other samples as background.

VP1 of AAV8 were used in these experiments because AAV8 was used in the CRISPR screen and allowed the comparison of potential hits in both methods (e.g., it would not be appropriate to compare two different serotypes). AAP2 was used because it robustly trans-complements AAV8 production (Maurer et al., 2018, supra; Earley et al, 2017, J. Virol., 91(3):doi: 10.1128/JVI.01980-16; Grosse et al., 2017, J. Virol., 91(20):doi: 10.1128/JVI.01198-17; Sonntag et al., 2011, J. Virol., 85:12686-97) and because, since no cellular binding partners for AAP have been identified from any serotype to date, AAP2 has been studied in deepest detail and will better inform the conclusions and hypotheses regarding AAP interactions with cellular proteins.

Figure 7A:
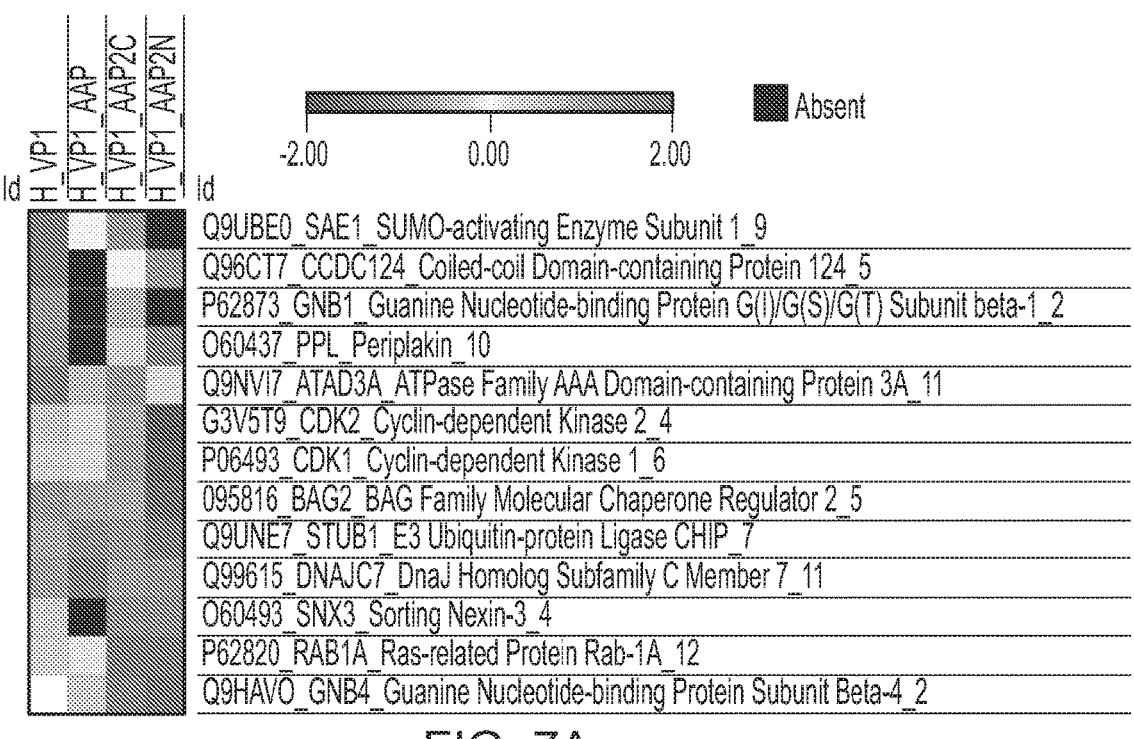
FIGS. 7A and 7B are heat maps showing co-precipitated proteins identified by mass spectrometry.
Figure 7B:
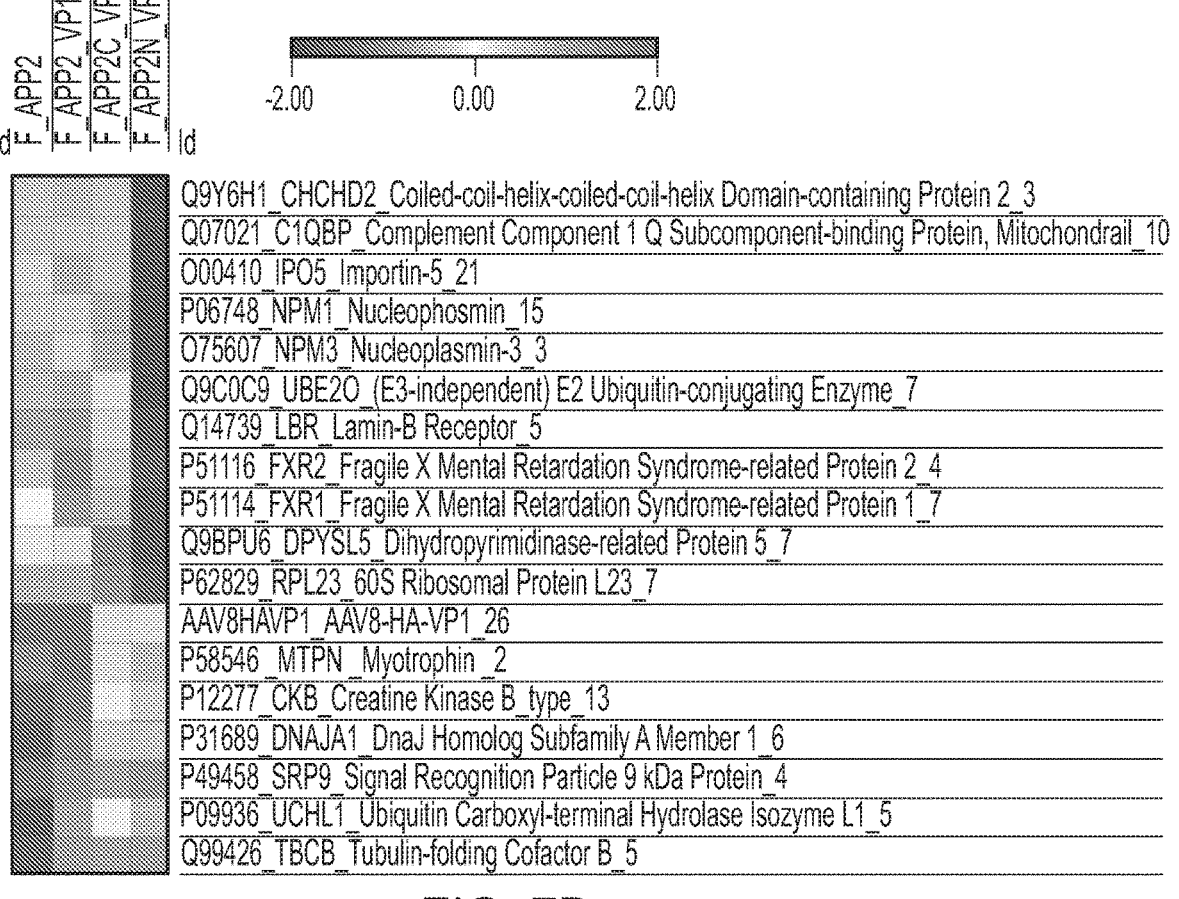

Biological duplicates of each transfection and immunoprecipitation (FIG. 6) were performed, and differential banding could be observed between pulldowns (FIGS. 6D and 6F), indicating that unique cellular proteins were present in each condition. LC-MS/MS was performed on the elutions, and the proteins that were statistically significantly enriched under each condition, normalized to bait proteins, are summarized in the heat maps shown in FIG. 7A (the proteins that were pulled down for HA-VP1 and, thus, shows binding partners of VP1) and 7B (the proteins that were pulled down for FLAG-AAP2 and, thus, shows the binding partners of AAP2). Row names in FIGS. 7A and 7B include the Uniprot accession number, gene symbol, protein name, and the number of unique peptides identified for that gene product. Column identifiers in FIGS. 7A and 7B include the tagged bait protein and other viral proteins expressed in each condition (as diagrammed in FIG. 6).

The binding partners identified represent a unique set of proteins from those identified previously in vector preparations. Moreover, proteins co-precipitated by VP differ from those in AAP pulldowns, and this set changes depending on co-expression of viral proteins. For example, VP1 co-precipitates Bag2, STUB1, and DnaJC7, unless full-length AAP or AAPN are co-expressed. Conversely, AAP co-precipitates DnaJA1 only when VP1 is co-expressed, indicating that DnaJA1 association with VP1 is dependent on AAP. These four proteins are co-factors of the ubiquitously expressed heat shock cognate 70 and heat shock protein 70 (Hsc/Hsp70), essential chaperone proteins that directly catalyze protein folding. While Hsp70 was detected in the pulldowns, true enrichment in specific pulldowns is difficult to determine because of the incredibly high expression levels of Hsp70 in HEK293 cells, heightening background levels and making nonspecific binding events a more frequent occurrence.

There are also proteins whose interactions with VP or AAP are not heavily influenced by the presence of each other. The nucleolar-enriched protein Nucleophosmin, which has been shown to interact with intact capsids (Dong et al., 2014, PLoS One, 9:e86453) and be required for their nuclear/nucleolar translocation during infection (Bevington et al., 2007, Virology, 357:102-13; Johnson and Samulski, 2009, J. Virol., 83:2632-44), was co-precipitated by full-length AAP2 in the presence and absence of VP1, and, more specifically, by AAPC and not by AAPN. Importin-5, a member of the importin-beta family responsible for mediating translocation through the nuclear pore complex, showed a similar pattern to Nucleophosmin, binding AAP (and AAPC, but not AAPN) regardless of the presence of VP. Importin-beta has been shown to co-localize with incoming AAV2 particles, but specific members of the family were not investigated (Nicolson and Samulski, 2014, J. Virol., 88:4132-44). These results suggest that AAP's nuclear/nucleolar transportation and the co-transport of VP proteins for assembly in nucleoli are mediated through C-terminal sequences of AAP. Indeed, the nuclear and nucleolar localization signals described for AAP2 are in the C-terminal portion (Earley et al., 2014, J. Virol., doi: 10.1128/jvi.03125-14). Another class of proteins co-precipitated by AAP were not pulled down unless VP1 is co-expressed, such as Creatine Kinase B and Myotrophin. These and many other proteins identified by the MS approach described herein have heretofore not been implicated in AAV's replication cycle. Some of the binding partners identified are poorly characterized genes/proteins, such as FXR1 and FXR2.

Example 4—Functional Assessment of Select Hits by Chemical Inhibition

As a first pass to validate binding partners' influence on vector production, all hits for which chemical inhibitors are commercially available were tested. In addition, Bafilomycin A1 was tested; Bafilomycin A1 inhibits the vacuolar-specific H+ ATPase, of which five subunits were identified as highly depleted in the CRISPR screen (FIGS. 2 and 3). Bafilomycin A1 also was shown to rescue VP protein in the absence of AAP (Maurer et al., 2018, supra).

Figure 8A:
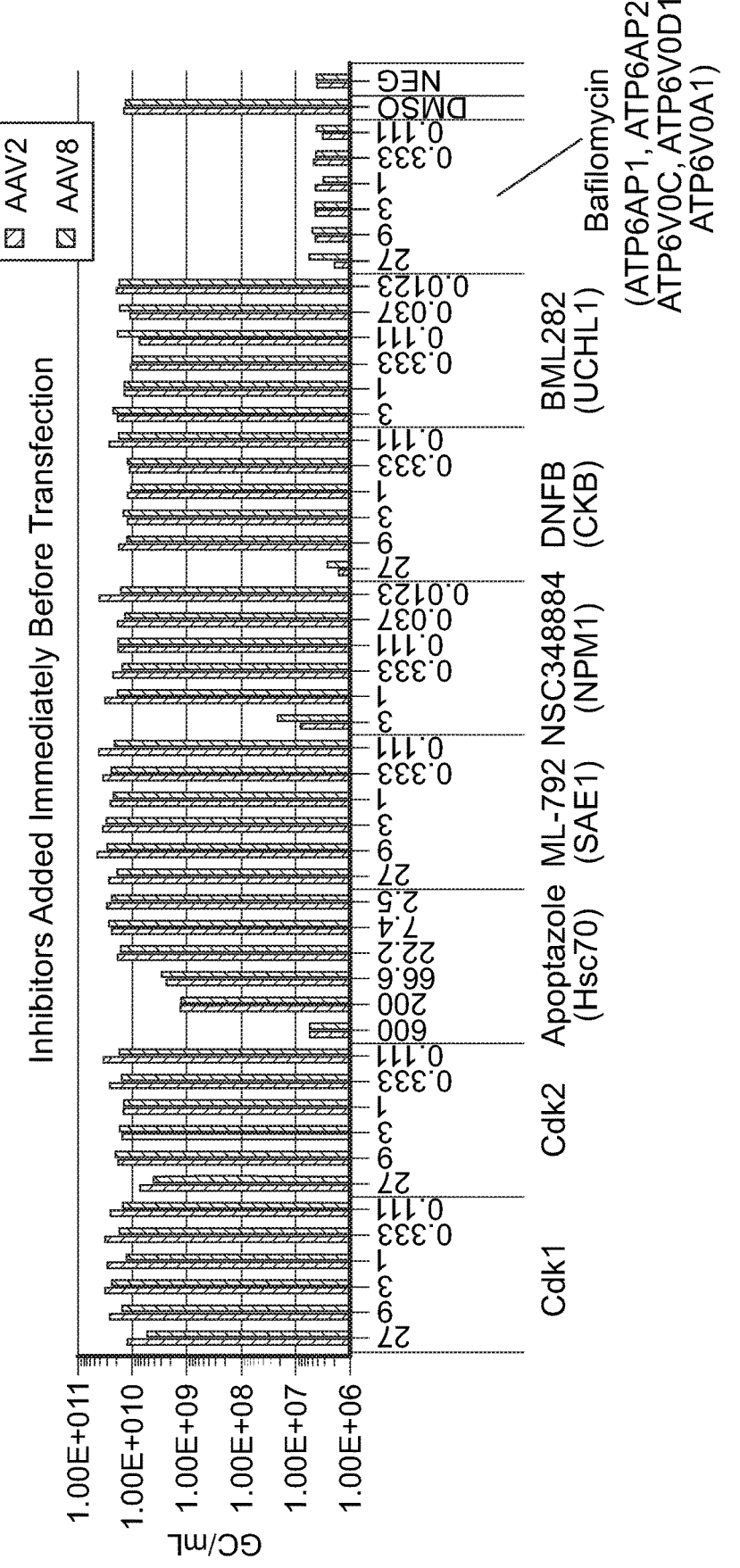
FIG. 8A is a bar graph that shows the effect of pharmacological inhibition of select host factors on vector production when added immediately before transfection.
Figure 8B:
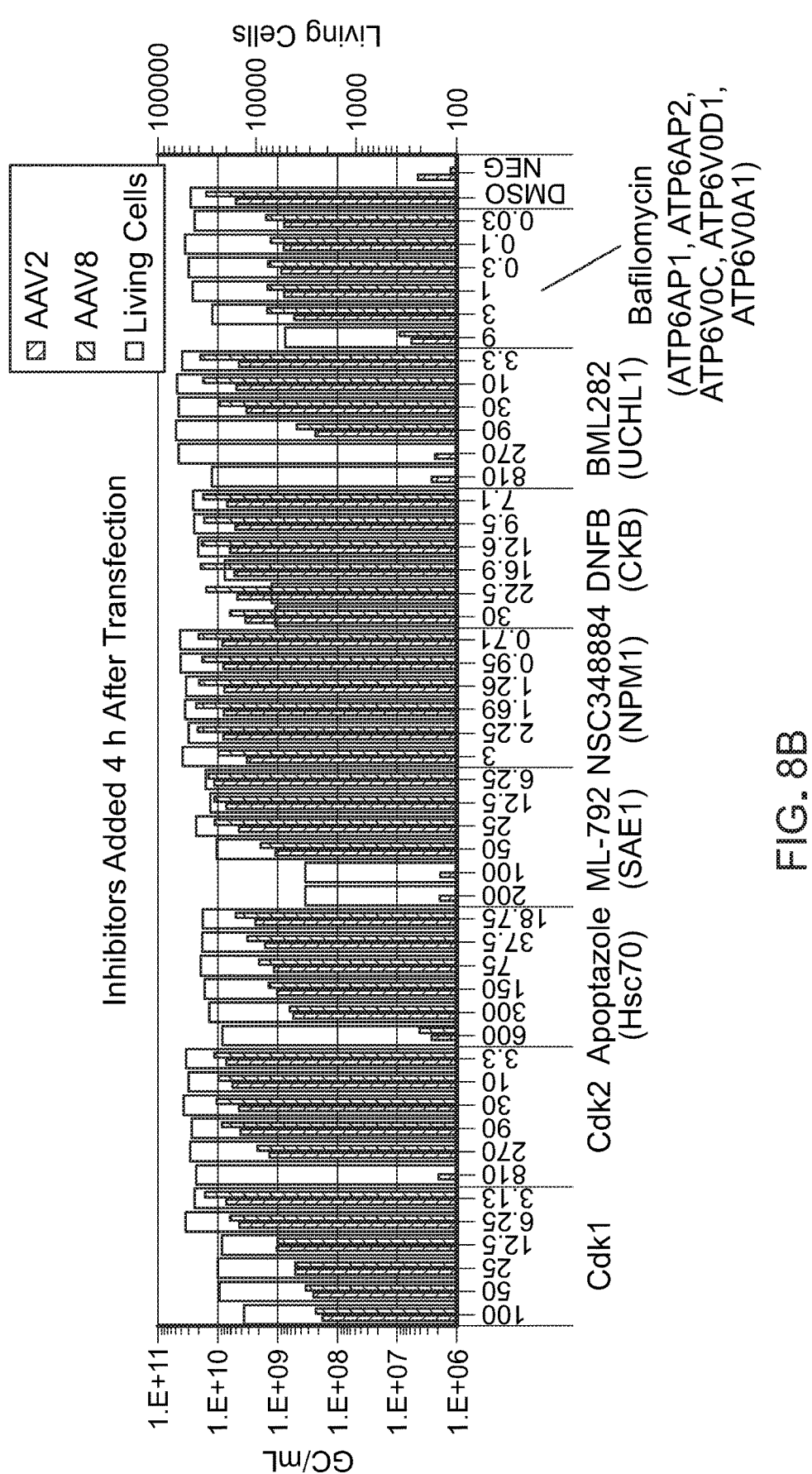
FIG. 8B is a bar graph that shows the effect of pharmacological inhibition of select host factors on vector production when added 4 hours after transfection.

Inhibitors were serial diluted in media at a range of concentrations centered at the manufacturer's suggested dosage for cultured cells. Inhibitor-containing media was added to wells and transfection mixtures containing either AAV2 (light bars) or AAV8 (dark bars) production plasmids were added dropwise on top, and vector harvested 48 h later (FIG. 8A). Inhibition of Hsc/Hsp70, Nucleophosmin, and Creatine Kinase B at the highest dose and Bafilomycin A1 at all doses abolished vector production to background levels. To examine whether any of these were not directly inhibiting capsid assembly but rather a result of poor transfection efficiency, an upstream but important factor for vector production, the experiment was repeated adding inhibitors 4 h after transfection mixture was added to allow transfection steps to initiate (FIG. 8B).

The X-axis shows the concentrations of the inhibitors (in μM) in DMEM+10% FBS. Positive control transfections received DMSO only (DMSO), and negative control received DMSO and empty plasmid instead of cap gene to assess assay background (NEG). Crude vector preps were harvested 48 h after transfection and DRP quantified by qPCR. Viable cells were assayed at 48 h with Cell Titer Glow kit and values were plotted using a standard curve of cells plated at two-fold dilutions in the same plate. General transfection efficiency was assessed visually by imaging EGFP positive cells (EGFP is present in the ITR-flanked transgene plasmid), and cell health was assessed visually by brightfield imaging and quantitatively by ATP levels in drug treated wells (light shading, FIG. 8B). Additionally, some concentrations of inhibitors were adjusted based on their ineffectiveness in the first experiment, and some of these concentrations may have exceeded doses that ensure specificity to the target enzyme.

The results of the second replicate of the experiment are presented for each inhibitor individually, normalized to living cell count, and with the corresponding microscopy images, in FIG. 9-FIG. 16. In these experiments, production plasmids were transfected into HEK293 cells and the appropriate inhibitor was serial diluted and added 4 h later at the concentrations indicated along the x-axis. The inhibitor was added at the same concentrations to a parallel plate and ATP levels were quantified by Cell Titer Glo® to assess cell viability after 48 h of incubation. General transfection efficiency (EGFP; present on ITR-flanked transgene plasmid) and cell morphology (Brightfield), at concentrations listed along the x-axis, were assessed by microscopy at 48 h, immediately before vector harvest from the same well. AAV2 (light bars) and AAV8 (dark bars) vector titer was quantified by qPCR on DRP. The number of genome copies (GC) in each prep were normalized to the number of living cells determined for each condition, and GC per living cell is reported as a percentage of the positive control transfections that received no inhibitor (DMSO). The pre-normalization data for these experiments are presented in FIG. 9B.

Figure 9:
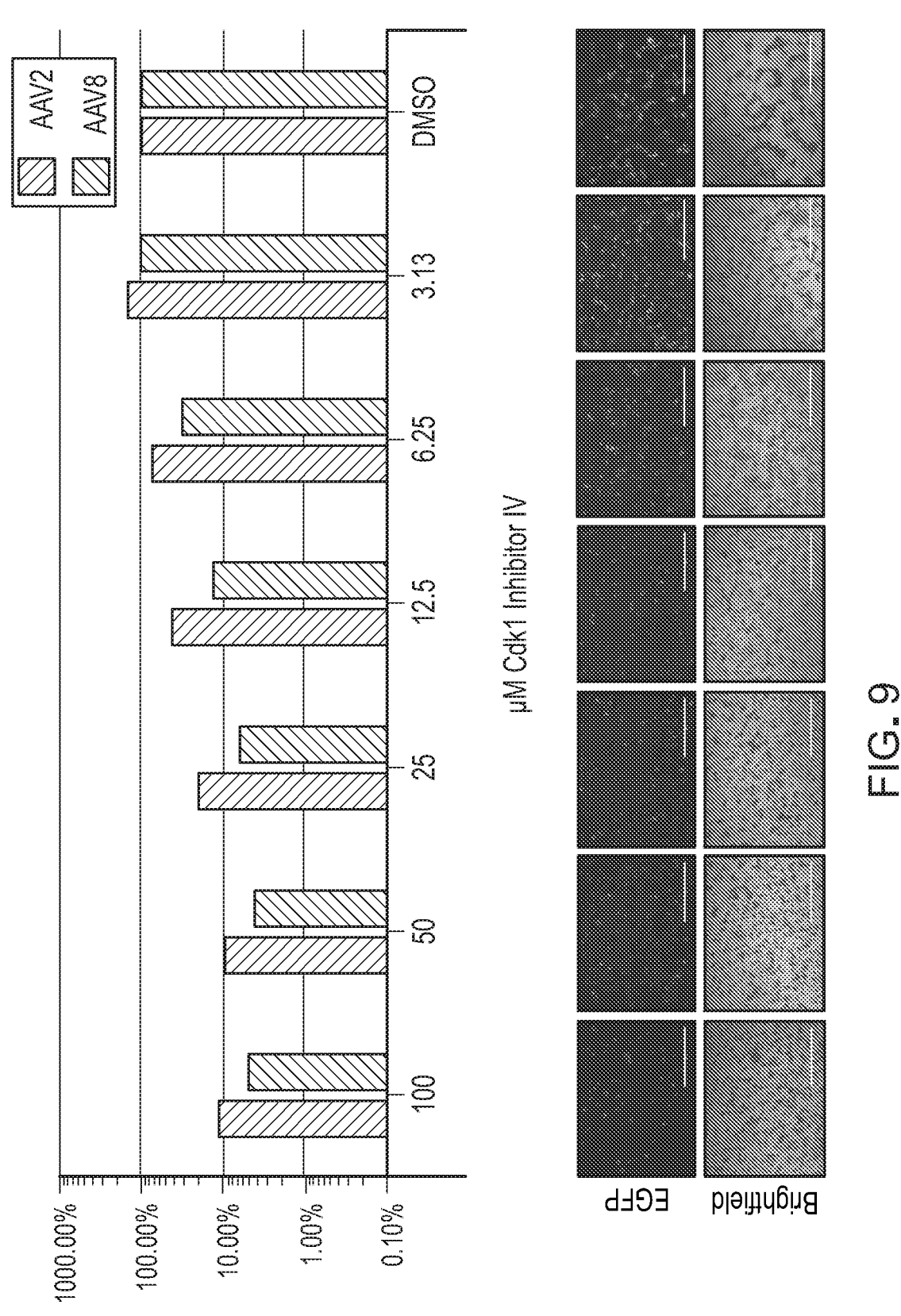
FIG. 9 is a bar graph (top) based on the experimental data (bottom) showing the effects of cyclin dependent kinase 1 inhibition 4 hours post transfection.

Cdk1 inhibition, by Cdk1 inhibitor IV, did not affect vector titer without concomitant decreases in both cell health and transfection efficiency (FIG. 9). Thus, a potential role for Cdk1 in vector production can neither be confirmed nor denied based on these experiments. An appreciable decrease on AAV8 titer without affecting cell viability was seen for AAV8 at 6.25 μM only when the inhibitor was added 4 h after transfection, but this concentration had no effect on AAV2 production. Considering that Cdk1 was identified as a potential binding partner using AAV8's VP1 as bait, this may suggest a serotype specific preferential interaction with AAV8 over AAV2.

Figure 10:
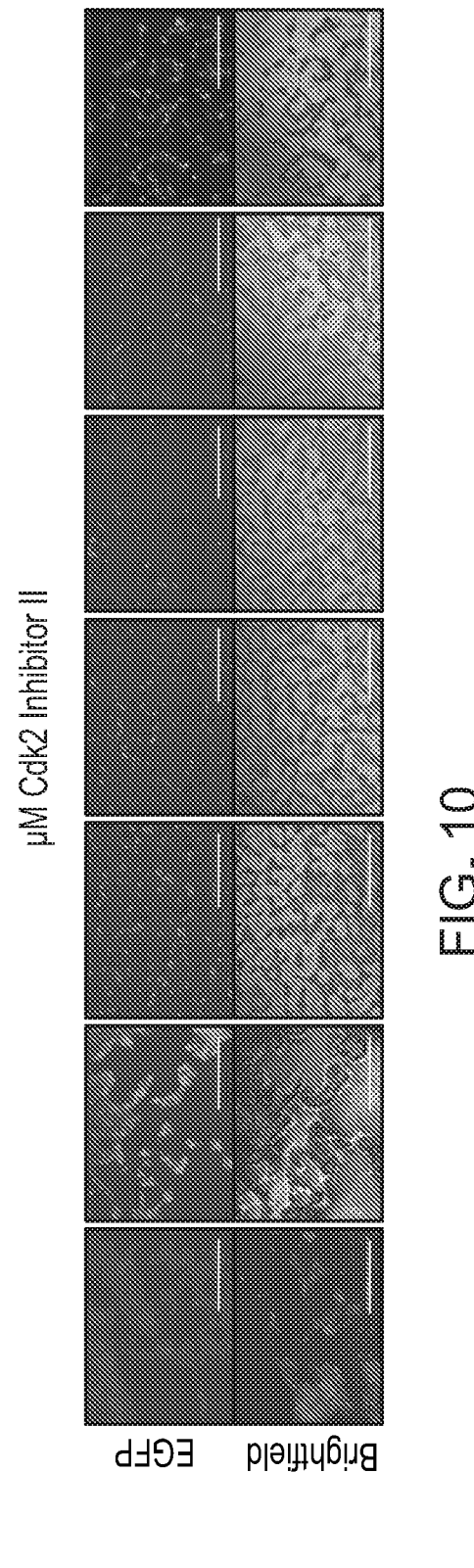
FIG. 10 is a graph (top) based on the experimental data (bottom) showing the effects of cyclin dependent kinase 2 inhibition 4 hours post transfection.

Cdk2 inhibition, by Cdk2 inhibitor II, showed a dose-dependent effect on both AAV2 and AAV8 production at higher concentrations, particularly 90-270 uM, without affecting cell viability (as assayed by ATP) or gross transfection efficiency (by EGFP visualization) (FIG. 10). Cell morphology was affected at 270 uM dosages, with apparently viable, GFP+ cells clumping together toward the center of each well. The near 10-fold decrease in AAV8 titer suggests a role for Cdk2 in production, but further experimentation is necessary to rule out any non-specific effects at these higher drug concentrations.

Figure 11:
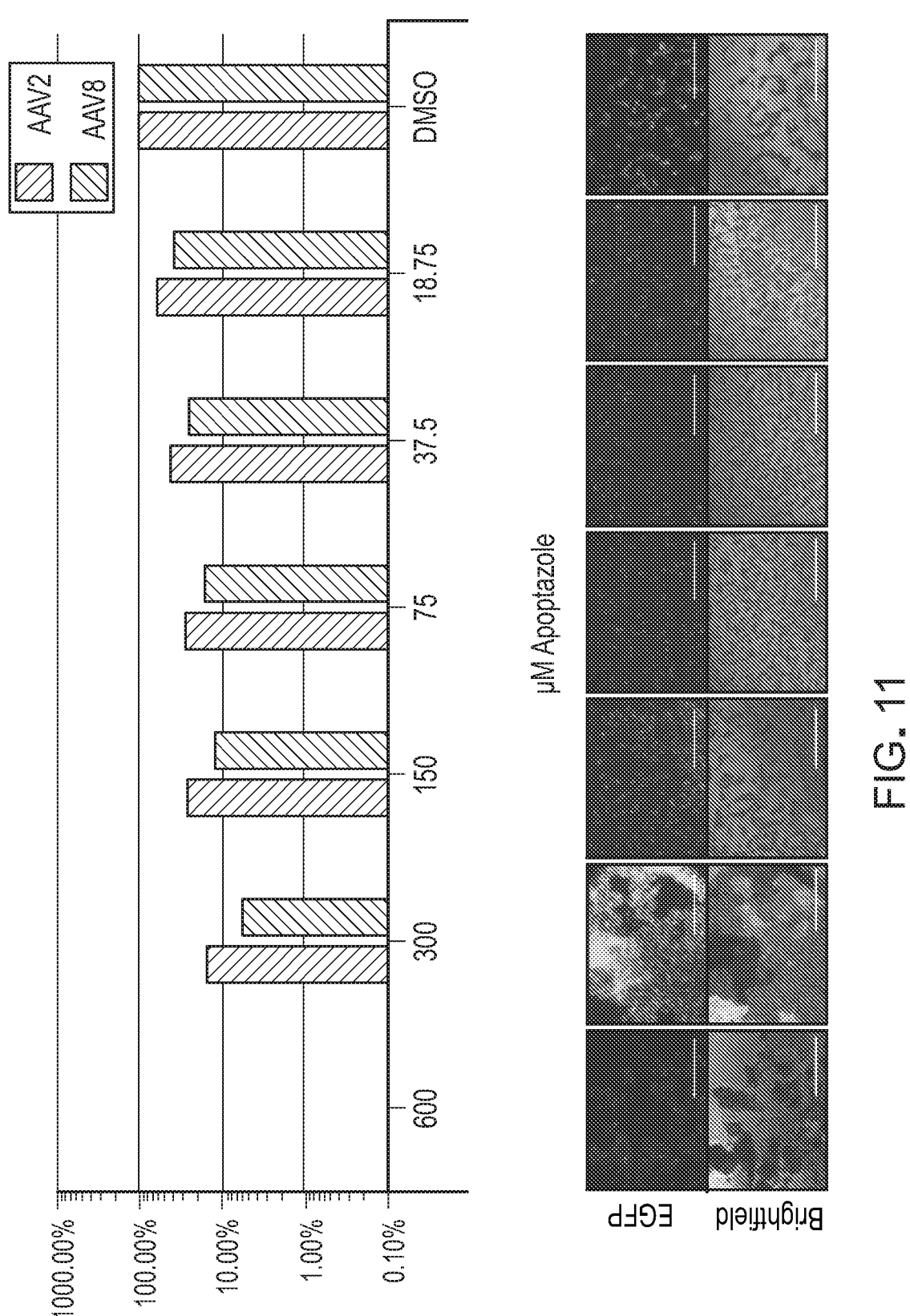
FIG. 11 is a graph (top) based on the experimental data (bottom) showing the effects of heat shock protein 70 inhibition 4 hours post transfection.
Figure 12:
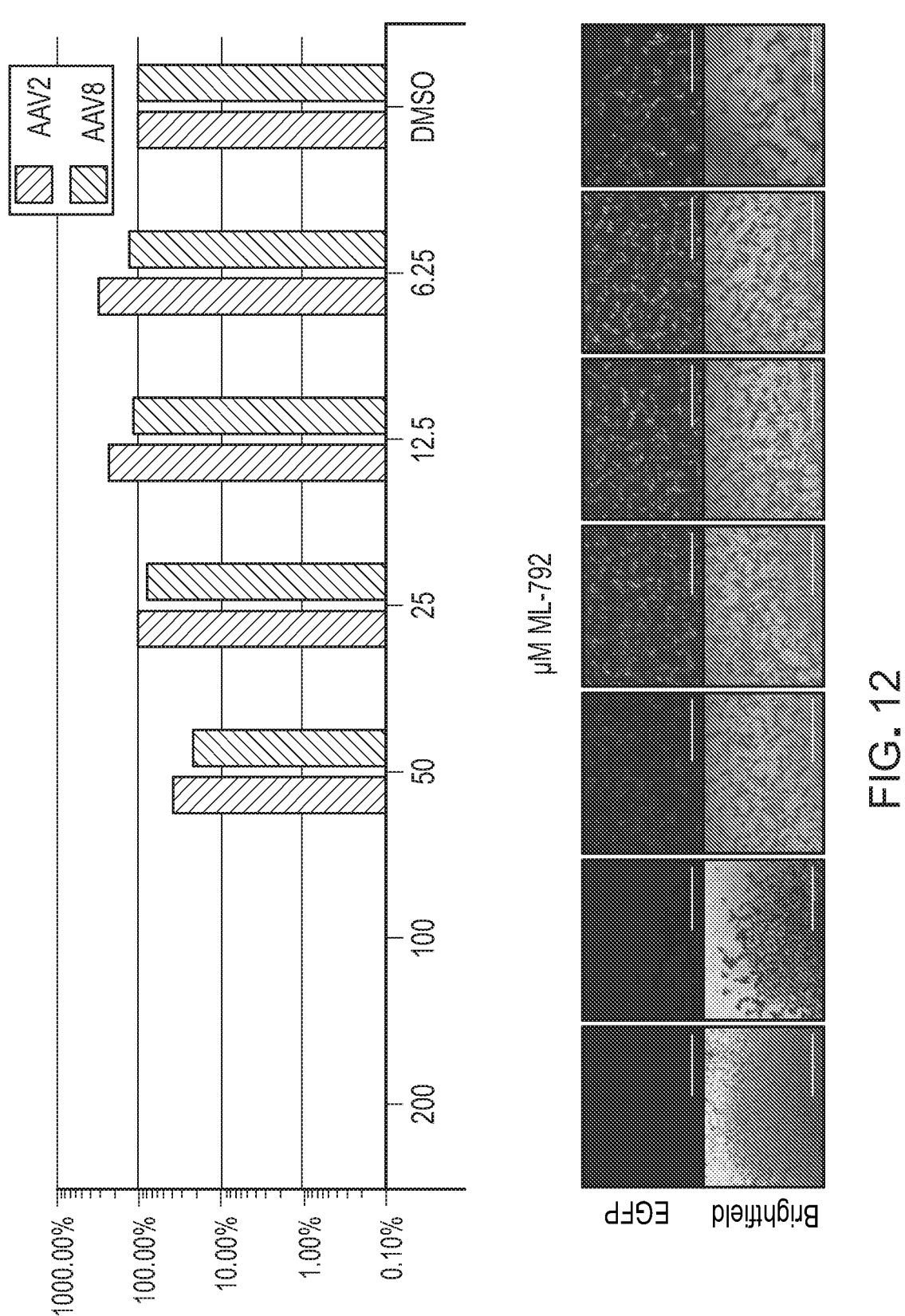
FIG. 12 is a graph (top) based on the experimental data (bottom) showing the effects of sumo-activating enzyme 1 inhibition 4 hours post transfection.
Figure 13:
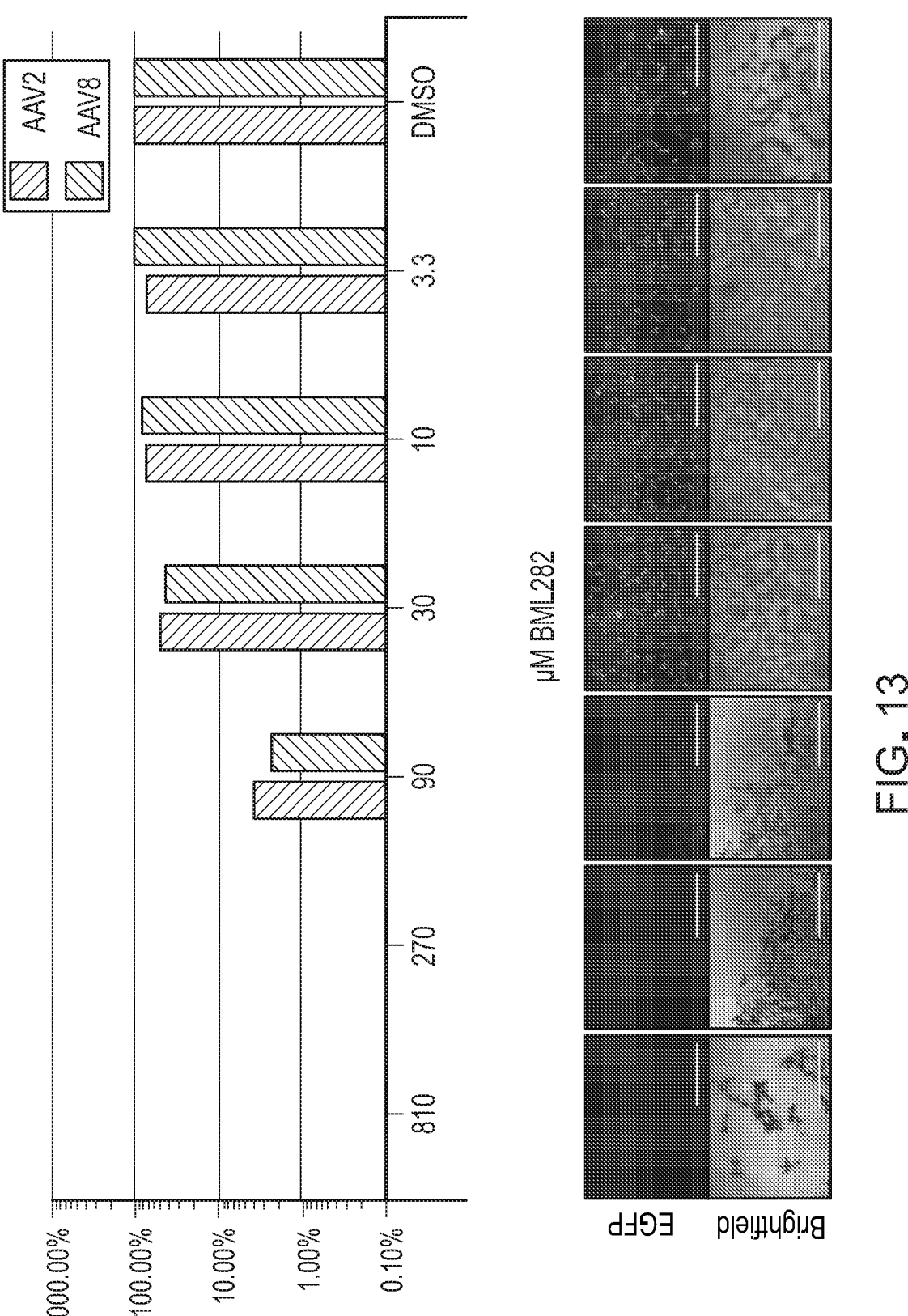
FIG. 13 is a graph (top) based on the experimental data (bottom) showing the effects of ubiquitin carboxyl terminal hydrolase isoenzyme L1 inhibition 4 hours post transfection.

There are no commercially available inhibitors against Bag2, STUB1, DnaJC7, or DnaJA1, however apoptazole inhibits the chaperones, Hsc70 and Hsp70, through which all four of these co-chaperones are reported to function. Hsc/Hsp70 inhibition, by apoptazole, shows a strong dose dependent decrease in vector production (down to 5% for AAV8) with no apparent loss in transfection efficiency, but with drastic changes in cell morphology (FIG. 11). At 300 uM, the cells clustered together toward the center of the well but still exhibited robust expression of EGFP and did not show appreciable cell death as assayed by ATP abundance. Of course, inhibition of this chaperone, which is critical to the folding of a significant proportion of cellular proteins, may be indirectly affecting other machinery required for production. Further studies are required to confirm Hsc/Hsp70's direct role in folding VP, but it's clear from these results that Hsc/Hsp70-related functions are critical for production.

Inhibition of SAE1, by ML-792 (FIG. 12), or UCHL1, by BML282 (FIG. 13), had significant effects on vector titer, but they were concomitant with a dramatic loss in EGFP expression. Thus, it's possible that the effects on titer are a result of poor transfection.

Figure 14:
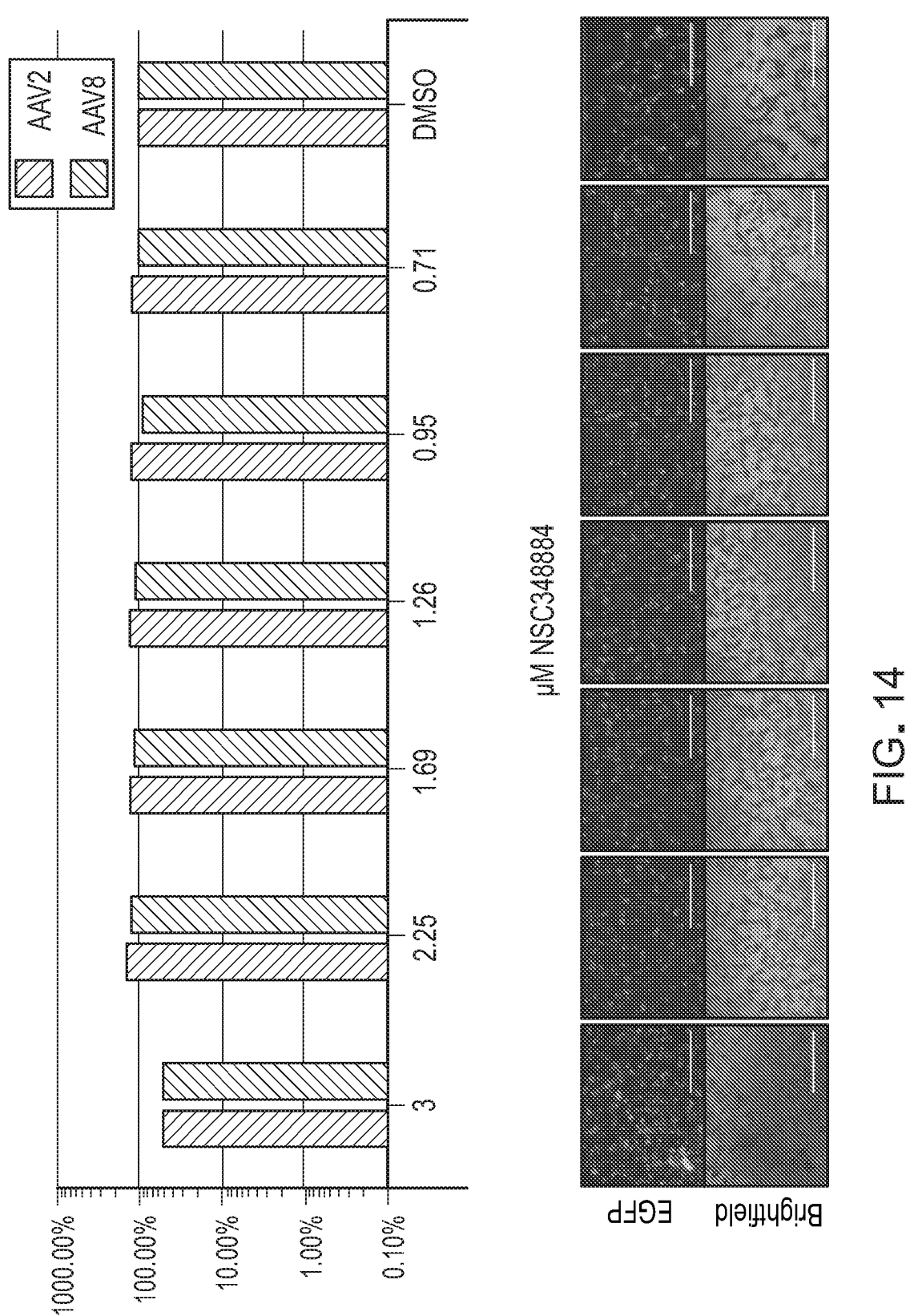
FIG. 14 is a graph (top) based on the experimental data (bottom) showing the effects of nucleophosmin inhibition 4 hours post transfection.
Figure 15:
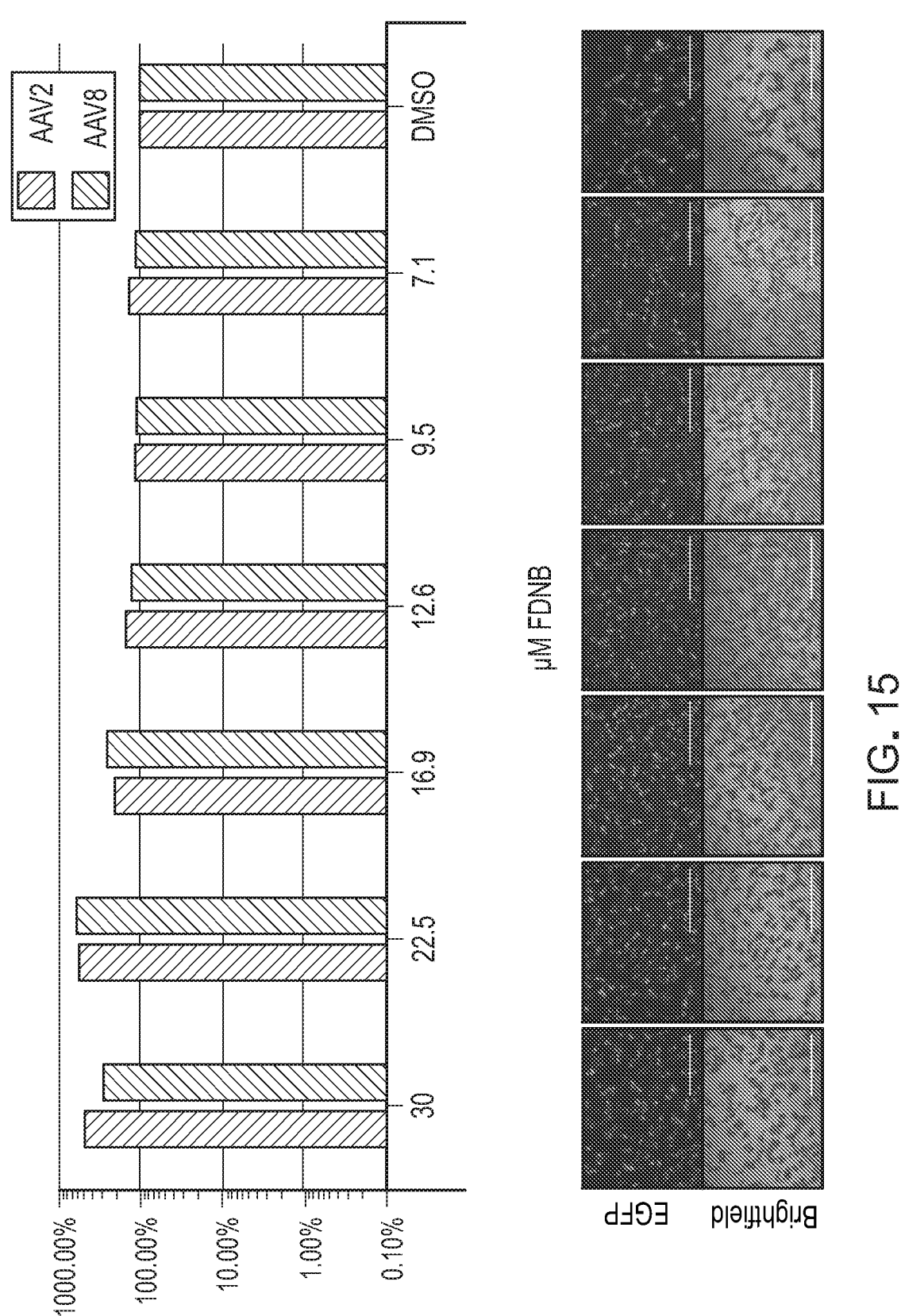
FIG. 15 is a graph (top) based on the experimental data (bottom) showing the effects of creatine kinase B inhibition 4 hours post transfection.

Nucleophosmin (NPM1) has roles as both a folding and nuclear/nucleolar transport chaperone, particularly in the context of ribosome biogenesis. NPM1 has been shown previously to interact with Rep proteins and with assembled capsids, but the experimental design of these studies would not have addressed AAP-NPM1 interactions (Dong et al., 2014, PLoS One, 9:e86453; Bevington et al., 2007, Virology, 357:102-13). Pharmacological inhibition of NPM1, by NSC348884, immediately before transfection had a large effect on vector titer (FIG. 8A), but this effect was not seen when added 4 h after transfection (FIG. 8B and FIG. 14). This suggests a very early role for NPM1.

Creatine Kinase B (CKB) plays important roles in metabolism, specifically as an in situ regenerator of cellular ATP in sites where it is rapidly consumed. Inhibition of CKB, by FDNB, appears to increase per cell vector production (FIG. 15), but it is likely that this is a function of quantifying viable cells indirectly by measuring ATP levels; inhibiting ATP regeneration thus results in an artifactually low viable cell counts and, therefore, higher genome copies per living cell.

Figure 16:
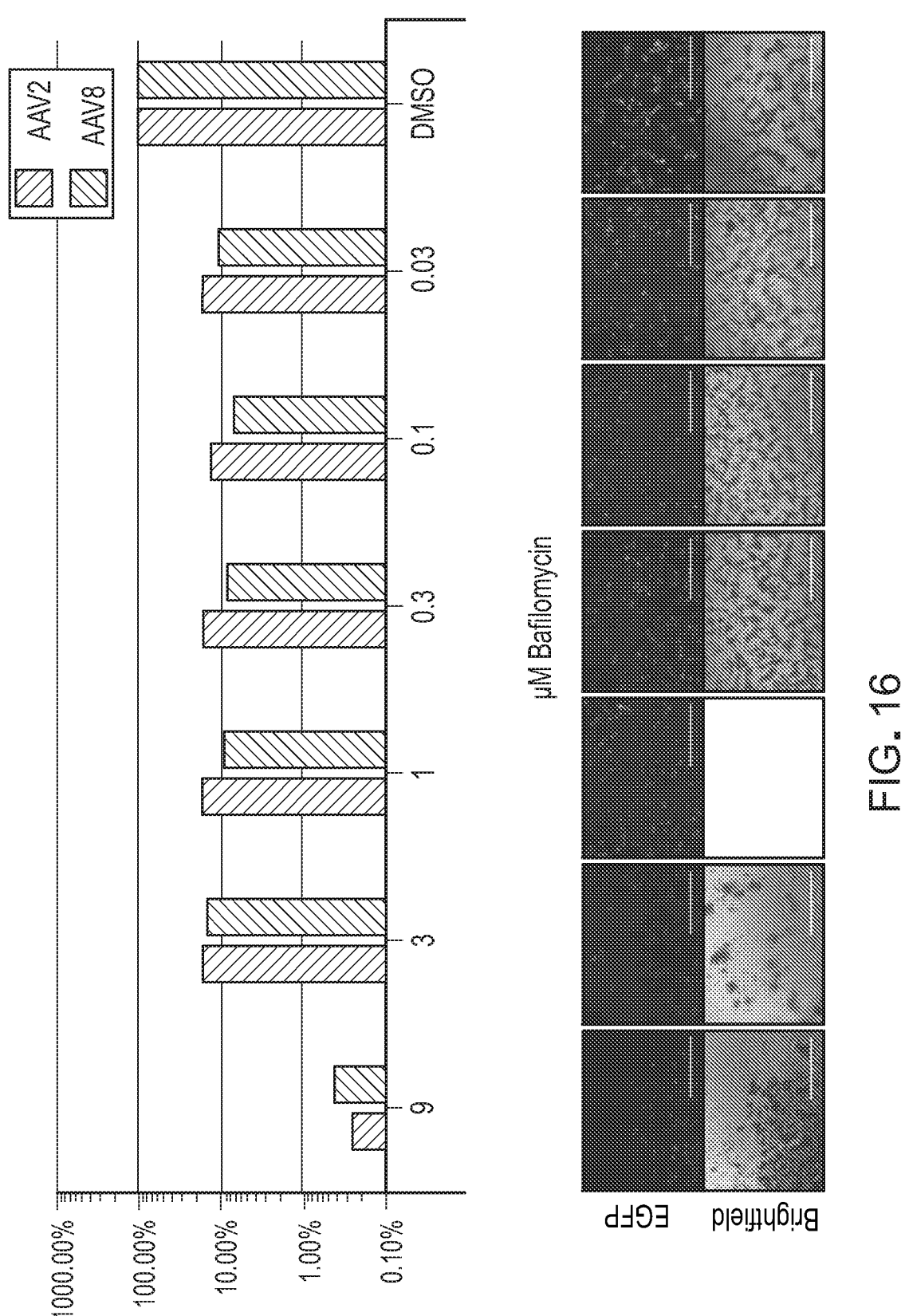
FIG. 16 is a graph (top) based on the experimental data (bottom) showing the effects of vacuolar H+ ATPase inhibition 4 hours post transfection.

The vacuolar-specific H+ ATPase (V-ATPase) is a multi-subunit enzymatic complex that catalyzes the translocation of protons across membranes of subcellular compartments, affecting the interior pH. The V-ATPase is important for acidification of the lysosome, the endosome and the autophagosome, and inhibition of the V-ATPase by Bafilomycin A1 blocks AAV infection (Bartlett et al., 2000, J. Virol., 74:2777-85; Sonntag et al., 2006, J. Virol., 80:11040-54). Bafilomycin A1 also blocks PEI-mediated transfection of plasmid DNA (You and Auguste, 2010, Biomater., 31:6859-66), which explains the abolished vector production seen when V-ATPase is inhibited immediately before transfection (FIG. 8A) and depletion of the subunits from the genome-wide CRISPR knockout screen (FIGS. 2 and 3). When Bafilomycin A1 is added 4 h post transfection at low doses, a 10-fold reduction was observed in vector titer with no visibly appreciable effect on transfection efficiency (FIG. 16). Bafilomycin A1 treatment rescues degradation of some serotype's VP proteins in the absence of AAP (Maurer et al., 2018, supra), implicating the acidification of digestive organelles to have antagonistic effects on AAV production. However, in the presence of AAP, such as in (Sonntag et al., 2011, J. Virol., 85:12686-97), this acidification also appears to be critical for production. These results suggest that the endosomal, lysosomal, and/or autophagosomal compartments have complex roles in all phases of the AAV replication cycle and in the recombinant vector production setting.

Example 5—Proposed Model

Figure 17:
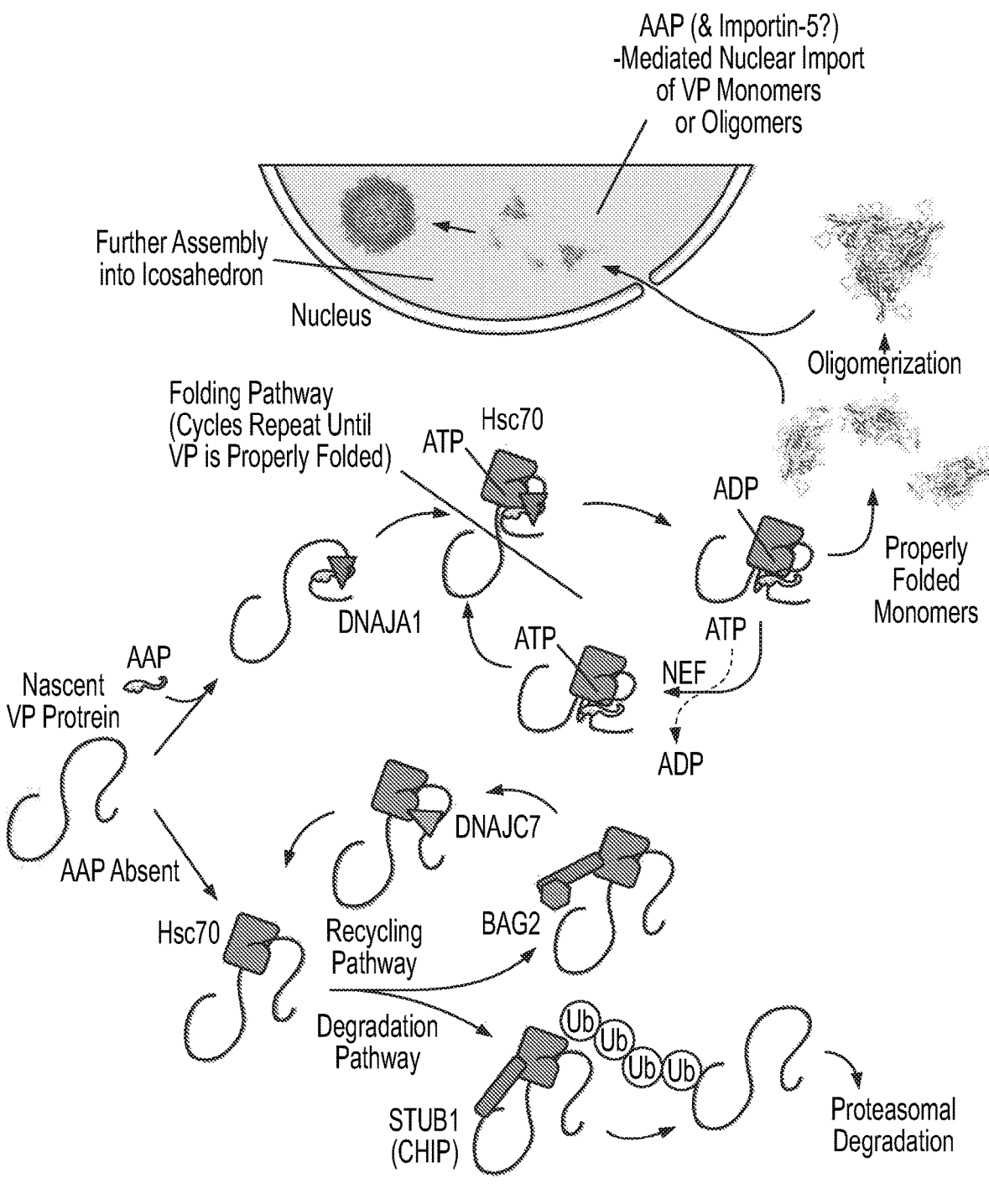
FIG. 17 is a schematic showing a hypothetical model of AAV assembly.

FIG. 17 is a schematic showing a hypothetical model of AAV assembly that incorporates a number of proteins of interest. Nascent VP proteins (far left), translated in the cytoplasm, are proteasomally degraded in the absence of AAP. With AAP present, VPs oligomerize into assembly intermediates and are transported into the nucleus to complete capsid assembly. It is unknown whether AAP co-transports VPs as monomers or oligomers. All of the other proteins shown in the diagram were identified in the series of pulldowns and assembled here in a hypothetical mechanism based on their presence or absence in samples (e.g., FIG. 7) and based on their known function from the literature.

The genome-wide CRISPR knockout screen yielded at least two hits with very high statistical significance—ATF7IP and SETDB1—in both the 18 h and 24 h samples. These proteins exist together in the HUSH complex, a repressive chromatin modifier that trimethylates H3K9 to silence transcriptionally active loci, and these proteins are functionally co-dependent (24). A model where the HUSH complex silences expression of the viral proteins from the transfected plasmids is possible, or it could be that HUSH is silencing expression of other factors that promote capsid assembly.

The proteomics studies yielded a larger set of hits with statistical significance than the CRISPR screen, and, moreover, several hits that differentially bind viral proteins have roles that feed into different branches of the same pathway such as DnaJA1, DnaJC7, BAG2, and STUB1. Hsc/Hsp70 activity relies on co-chaperones, such as J-proteins, which stimulates ATP hydrolysis by Hsc/Hsp70 to increase substrate binding affinity, and the BAG family proteins that function as Nucleotide Exchange Factors. J-proteins also bind directly to their substrates, indicating a role for DnaJ proteins in Hsp70 substrate selectivity. Together, these co-chaperones and Hsc/Hsp70 can drive substrate folding, but also have roles in substrate degradation. STUB1 is an E3 ligase that acts as a negative regulator of protein stability by ubiquitinating Hsc/Hsp70 substrates that are incompletely or improperly folded to target them for proteasomal degradation. BAG2 stimulates Hsp70's ATPase activity in conjunction with DnaJ proteins and inhibits STUB1's ubiquitination activity. DNAJC7 has been implicated to have stabilizing roles by blocking proteasomal degradation of substrates and is proposed to act as a recycling chaperone by returning improperly folded substrates to earlier steps in the folding pathway. That VP1 associates differentially with DNAJA1, BAG2, and STUB1 in the presence and absence of AAP suggests a direct role for AAP in co-chaperone selectivity, interaction, and functionality with Hsc/Hsp70. Additionally, it proposes a functional network by which AAP acts upstream to block proteasomal degradation of VP proteins.

OTHER EMBODIMENTS

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method for improving the assembly of adeno-associated virus (AAV) in a cell, the method comprising:

increasing expression or activity of Hsc/Hsp70 or a co-factor thereof, vacuolar-specific H+ ATPase, and/or cyclin-dependent kinase 2 in the cell to produce a modified cell;

infecting the modified cell with an AAV vector to produce an infected modified cell;

culturing the infected modified cell; and collecting the assembled AAV.

2. The method of claim 1, wherein the amount of assembled AAV collected is greater than the amount of assembled AAV collected following AAV infection of a cell that lacks the modification.

3. The method of claim 1, wherein the method results in an increase in titer of the AAV as compared to a cell without an increase in expression or activity of Hsc/Hsp70 or a co-factor thereof, vacuolar-specific H+ ATPase, and/or cyclin-dependent kinase 2.

4. A method for improving the assembly of adeno-associated virus (AAV), the method comprising:

producing AAV from a modified cell with the AAV, wherein the cell has been modified to exhibit an increase or decrease in one or more genes or the protein encoded therefrom selected from CHMP7, CEP72, CNOT6, SLC9A6, PPHLN1, ATF7IP, SETDB1, GPR89B, KIF16B, ATAD3A, BAG2, STUB1, DNAJA1, DNAJC7, HSPA8, HSPAIA, CDK1, CDK2, CHCHD2, C1QBP, DPYSL5, FXR1, FXR2, IPO5, LBR, MTPN, NPM3, NPM1, PPL, SNX3, UBE2O, SAE1, CCDC124, GNB1, RABIA, GNB4, RPL23, CKB, SRP9, UCHL1, and TBCB; and collecting the assembled AAV.

5. The method of claim 4, wherein the modified cell is a genetically engineered cell.

6. The method of claim 5, wherein the genetically engineered cell comprises knockout, knockdown, over-expression, or combinations thereof.

7. The method of claim 4, wherein the modified cell comprises a chemical compound that increases or decreases the one or more genes or the proteins encoded therefrom.

8. The method of claim 7, wherein the chemical compound is selected from the group consisting of Cdk1 inhibitor IV, Cdk2 inhibitor II, apoptozole, ML-792, BML282, NSC348884, FDNB, and Bafilomycin A1.

9. A cell-free culture system for assembling adeno-associated virus comprising:

culture media; and at least two proteins, or nucleic acids encoding the at least two proteins, selected from CHMP7, CEP72, CNOT6, SLC9A6, PPHLN1, ATF7IP, SETDB1, GPR89B, KIF16B, ATAD3A, BAG2, STUB1, DNAJA1, DNAJC7, HSPA8, HSPAIA, CDK1, CDK2, CHCHD2, C1QBP, DPYSL5, FXR1, FXR2, IPO5, LBR, MTPN, NPM3, NPM1, PPL, SNX3, UBE2O, SAE1, CCDC124, GNB1, RABIA, GNB4, RPL23, CKB, SRP9, UCHL1, and TBCB.

10. The cell free culture system of claim 9, comprising at least three proteins or nucleic acids encoding the at least three proteins.

11. A cell line comprising:

one or more mutations in Hsc/Hsp70 or a co-factor thereof, vacuolar-specific H+ ATPase, and/or cyclin-dependent kinase 2; and/or one or more exogenous constructs expressing Hsc/Hsp70 or a co-factor thereof, vacuolar-specific H+ ATPase, and/or cyclin-dependent kinase 2.

12. The cell line of claim 11, wherein the mutation comprises a knockout mutation.

13. The cell line of claim 11, wherein the mutation comprises a knockdown mutation.

14. The cell line of claim 11, wherein the one or more exogenous constructs is a recombinant construct.

15. An article of manufacture for improving the assembly of adeno-associated virus (AAV) in a cell, comprising at least one member from at least two of (a), (b) and of (c):

(a) Hsc/Hsp70 or a co-factor thereof, a nucleic acid encoding Hsc/Hsp70 or a co-factor thereof, or a compound that modulates Hsc/Hsp70 or a co-factor thereof;

(b) vacuolar-specific H+ ATPase, a nucleic acid encoding vacuolar-specific H+ ATPase, or a compound that modulates vacuolar-specific H+ ATPase; and (c) cyclin-dependent kinase 2, a nucleic acid encoding cyclin-dependent kinase 2, or a compound that modulates cyclin-dependent kinase 2.

16. The article of manufacture of claim 15, wherein the compound that modulates Hsc/Hsp70 or a co-factor thereof is apoptozole.

17. The article of manufacture of claim 15, wherein the compound that modulates vacuolar-specific H+ ATPase is Bafilomycin A1.

18. The article of manufacture of claim 15, wherein the compound that modulates cyclin-dependent kinase 2 is Cdk2 inhibitor II.

* * * * *